United States Patent
Lam et al.

(10) Patent No.: US 11,938,310 B2
(45) Date of Patent: Mar. 26, 2024

(54) MEDICAL DEVICE FLUSHING SYSTEMS AND METHODS

(71) Applicant: KARDIUM INC., Burnaby (CA)

(72) Inventors: Lok Tin Lam, Vancouver (CA); Saar Moisa, Vancouver (CA); Ashkan Sardari, North Vancouver (CA)

(73) Assignee: KARDIUM INC., Burnaby (CA)

(*) Notice: Subject to any disclaimer, the term of this patent is extended or adjusted under 35 U.S.C. 154(b) by 1093 days.

(21) Appl. No.: 16/777,361

(22) Filed: Jan. 30, 2020

(65) Prior Publication Data

US 2020/0282153 A1 Sep. 10, 2020

Related U.S. Application Data

(60) Provisional application No. 62/814,516, filed on Mar. 6, 2019.

(51) Int. Cl.
*A61M 25/00* (2006.01)
*A61B 18/00* (2006.01)
(Continued)

(52) U.S. Cl.
CPC ............ *A61M 5/36* (2013.01); *A61B 50/00* (2016.02); *A61B 50/36* (2016.02);
(Continued)

(58) Field of Classification Search
CPC ............ A61M 5/36; A61M 2210/125; A61M 2209/10; A61M 2005/1403; A61M 2025/0019; A61M 2005/1402; A61M 25/00; A61M 5/001; A61M 2005/006; A61M 2039/0018; A61M 2202/02;
(Continued)

(56) References Cited

U.S. PATENT DOCUMENTS 9,526,573 B2 12/2016 Lopes et al.
2018/0264225 A1* 9/2018 Sardari ................. A61M 25/00

OTHER PUBLICATIONS

Kottkamp et al. "Global multielectrode contact mapping plus ablation with a single catheter: Preclinical and preliminary experience in humans with atrial fibrillation." Journal of Cardiovascular Electrophysiology. 2017:1-10.

(Continued)

*Primary Examiner* — Robert J Utama
*Assistant Examiner* — Hamza A Darb
(74) *Attorney, Agent, or Firm* — ROSSI KIMMS & McDOWELL LLP

(57) ABSTRACT

A gas removal apparatus and a method for removing gas bubbles from at least a part of a medical device disposed in an interior chamber of a gas removal apparatus. The gas removal apparatus includes an interior chamber, a filling surface, a first opening arranged at an end of the filling surface and that provides a first path into the interior chamber, and a second opening that provides a second path into the interior chamber. When the apparatus is arranged in a liquid receiving position, at least a portion of the at least the part of the medical device is disposed above an uppermost surface of liquid in the interior chamber, and when the apparatus is arranged in another position different from the liquid receiving position, the entirety of the at least the part of the medical device is disposed below an uppermost surface of liquid in the interior chamber.

25 Claims, 10 Drawing Sheets

(51) Int. Cl.
   *A61B 18/08* (2006.01)
   *A61B 18/14* (2006.01)
   *A61B 18/16* (2006.01)
   *A61B 50/00* (2016.01)
   *A61B 50/36* (2016.01)
   *A61M 5/14* (2006.01)
   *A61M 5/36* (2006.01)

(52) U.S. Cl.
   CPC ... *A61B 2218/001* (2013.01); *A61B 2218/002* (2013.01); *A61B 2218/007* (2013.01); *A61M 2005/1402* (2013.01); *A61M 2005/1403* (2013.01); *A61M 25/00* (2013.01); *A61M 2025/0019* (2013.01); *A61M 2209/10* (2013.01); *A61M 2210/125* (2013.01)

(58) Field of Classification Search
   CPC ......... A61M 2202/03; A61B 2218/007; A61B 2218/002; A61B 2018/00267; A61B 2018/1467; A61B 50/00; A61B 50/36; A61B 2218/001; A61B 18/16; A61B 18/1492; A61B 18/082
   See application file for complete search history.

(56) References Cited

OTHER PUBLICATIONS

Mounsey. "A novel multielectrode combined mapping and ablation basket catheter: A future player in the atrial fibrillation ablation space?" Journal of Cardiovascular Electrophysiology. 2017:1-2.

\* cited by examiner

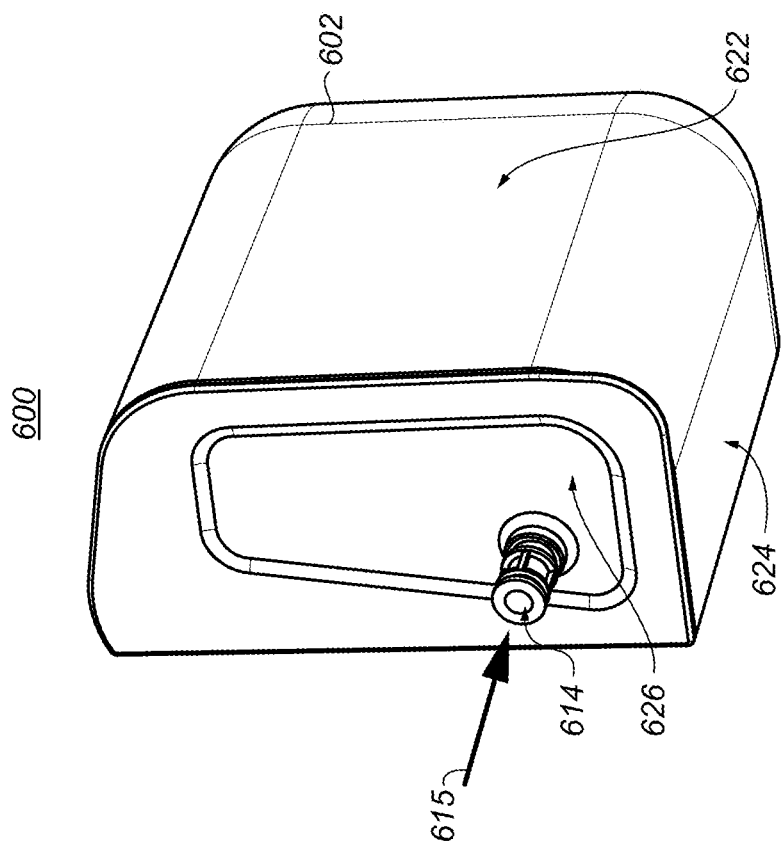
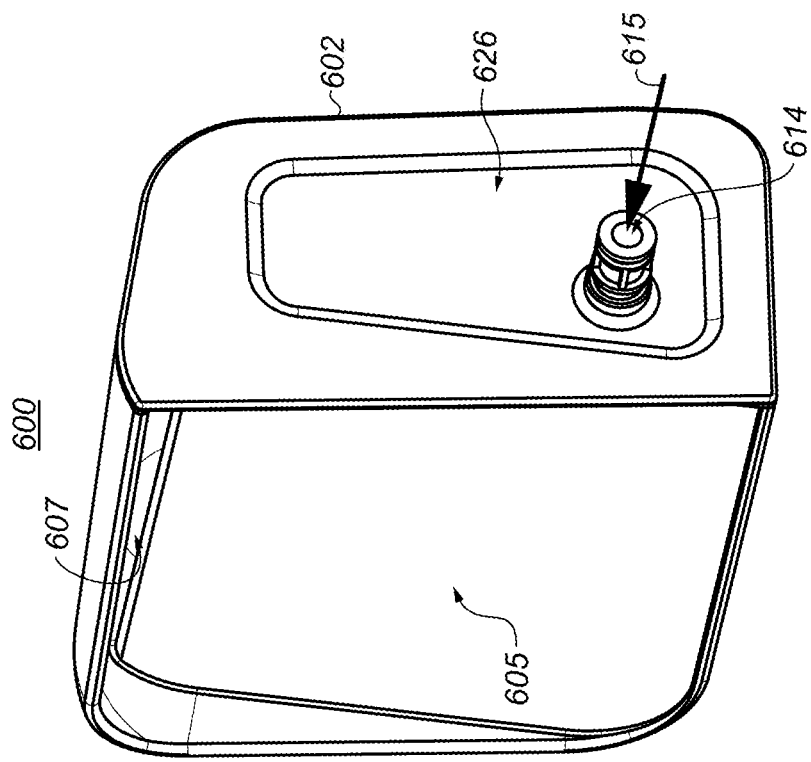

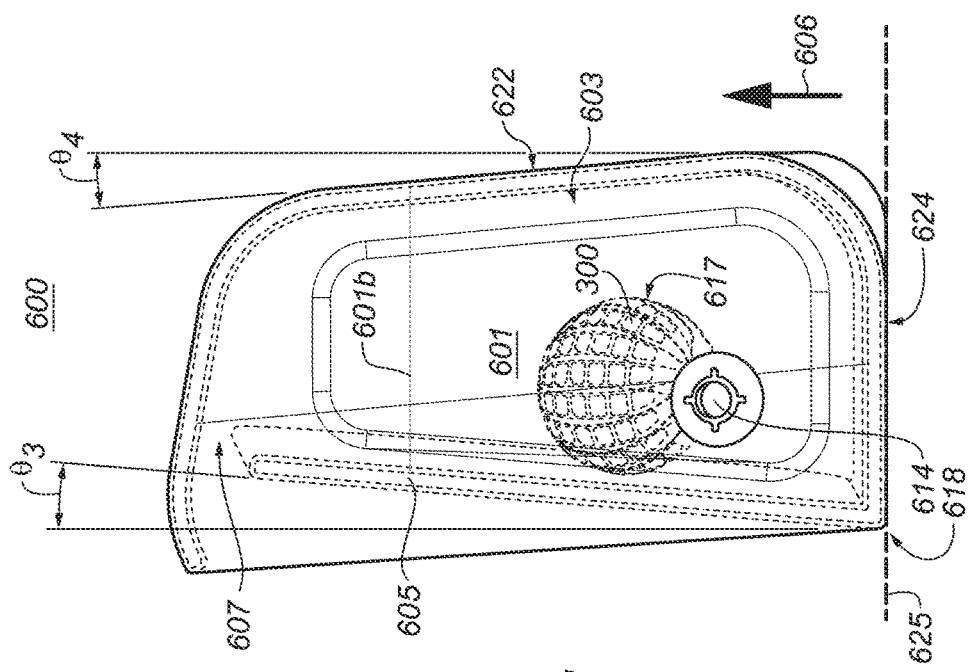
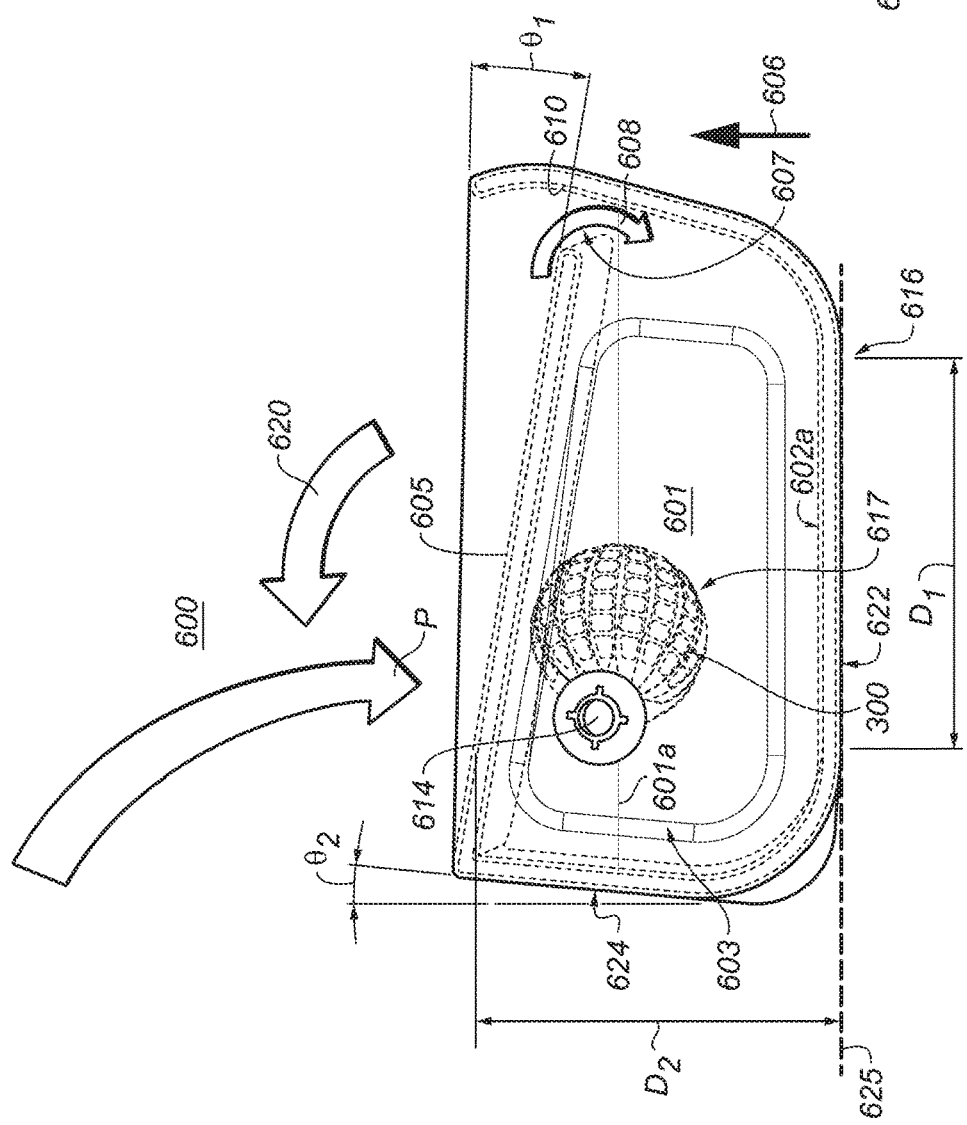
FIG. 4D
FIG. 4C

MEDICAL DEVICE FLUSHING SYSTEMS AND METHODS

CROSS-REFERENCE TO RELATED APPLICATION

This application claims the benefit of U.S. Provisional Application No. 62/814,516, filed Mar. 6, 2019, the entire disclosure of which is hereby incorporated herein by reference.

TECHNICAL FIELD

Aspects of this disclosure generally are related to apparatuses and methods for flushing a medical device system, such as a catheter device system, of an undesired fluid. According to some embodiments, apparatuses and methods are disclosed for flushing an undesired fluid from a controllable manipulable portion of a catheter device system.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications, and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During various procedures, health care providers create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy, and cryogenic techniques.

Preparation of catheter device systems for subsequent delivery through a bodily opening leading to a bodily cavity (e.g., as required by some percutaneous or intravascular procedures) may require that various fluids (e.g., air) be purged or otherwise removed from portions of the systems prior to insertion into the body. Failure to do so may allow for a transfer of at least some of the fluids to within the body which may in turn result in various undesired outcomes (e.g., the formation of various air embolisms). Various catheter device systems employ various features that can act as fluid traps from which undesired fluid may be difficult to remove therefrom. For example, various channels produced by various elements of a catheter member or medical instrument (e.g., converging elongated elements of basket-type catheter devices or converging members of various implants) may act as fluid traps. Even various materials that may be employed by various catheter device systems may make it difficult to remove undesired fluid. For example, polytetrafluoroethylene (PTFE) is typically employed by various catheter device systems because of its relatively low friction characteristics. However, polytetrafluoroethylene is an example of a material that essentially is hydrophobic in nature, and, thus, can restrict or hinder removal of fluid bubbles on a surface thereof when a water-based liquid (e.g., saline) is employed to flush or otherwise remove the fluid bubbles. That is, the flow of the flushing liquid may be insufficient to flush bubbles accumulated on a surface of the lumen, especially when that surface has hydrophobic characteristics which tend to repel the liquid, thereby reducing the flushing ability of the liquid.

Accordingly, a need in the art exists for systems and methods having improved capabilities for the removal of undesired fluid from medical device systems, such as catheter device systems.

SUMMARY

At least the above-discussed need is addressed and technical solutions are achieved in the art by various embodiments of the present invention.

According to some embodiments, a gas removal apparatus is provided. The gas removal apparatus may be configured to receive a first amount (e.g., a first volume or a first quantity) of liquid effective to remove gas bubbles from at least a part of a medical device removably disposed in the gas removal apparatus. In some embodiments, the gas removal apparatus may include an interior chamber configured to hold at least the first amount of liquid. In some embodiments, the gas removal apparatus may include a filling surface configured to receive the at least the first amount of liquid and cause the received at least the first amount of liquid to flow along the filling surface to the interior chamber when the gas removal apparatus is arranged in a liquid receiving position. In some embodiments, the gas removal apparatus may include a first opening arranged at an end of the filling surface. In some embodiments, the first opening may be configured to provide a first path into the interior chamber. In some embodiments, the filling surface may be configured such that the received at least the first amount of liquid that is caused to flow along the filling surface to the interior chamber, when the gas removal apparatus is arranged in the liquid receiving position, enters the interior chamber via the first path provided by the first opening. In some embodiments, the gas removal apparatus may include a second opening configured to provide a second path into the interior chamber, the second opening configured to receive the medical device such that the at least the part of the medical device enters the interior chamber via the second path provided by the second opening. In some embodiments, the first path into the interior chamber and the second path into the interior chamber are mutually exclusive paths into the interior chamber. In some embodiments, the gas removal apparatus may be configured such that, when arranged in the liquid receiving position in a state where (a) the at least the first amount of liquid is present in the interior chamber, and (b) the at least the part of the medical device protrudes into the interior chamber via the second opening and is positioned at a particular location and in a particular configuration in the interior chamber, at least a portion of the at least the part of the medical device is disposed above an uppermost surface of the at least the first amount of liquid present in the interior chamber. In some embodiments, the gas removal apparatus may be further configured such that, when arranged in another position different from the liquid receiving position in a state where (i) the at least the first amount of liquid is present in the interior chamber, and (ii) the at least the part of the medical device protrudes into the interior chamber via the second opening and is positioned at the particular location and in the particular configuration in the interior chamber, the entirety of the at least the part of the medical device is disposed below an uppermost surface of the at least the first amount of liquid present in the interior chamber.

In some embodiments, the gas removal apparatus may be further configured such that the second opening is disposed below the uppermost surface of the at least the first amount of liquid present in the interior chamber when the gas removal apparatus is arranged in the another position different from the liquid receiving position in the state where (i) the at least the first amount of liquid is present in the interior chamber, and (ii) the at least the part of the medical device protrudes into the interior chamber via the second opening and is positioned at the particular location and in the particular configuration in the interior chamber. In some embodiments, the gas removal apparatus may be further configured such that the second opening is disposed above the uppermost surface of the at least the first amount of liquid present in the interior chamber when the gas removal apparatus is arranged in the liquid receiving position in the state where (a) the at least the first amount of liquid is present in the interior chamber, and (b) the at least the part of the medical device protrudes into the interior chamber via the second opening and is positioned at a particular location and in the particular configuration in the interior chamber. In some embodiments, the gas removal apparatus may be further configured such that the first opening is disposed above the uppermost surface of the at least the first amount of liquid present in the interior chamber when the gas removal apparatus is arranged in the another position different from the liquid receiving position in the state where (i) the at least the first amount of liquid is present in the interior chamber, and (ii) the at least the part of the medical device protrudes into the interior chamber via the second opening and is positioned at the particular location and in the particular configuration in the interior chamber. In some embodiments, the gas removal apparatus may be further configured such that the first opening is disposed above the second opening when the gas removal apparatus is arranged in the another position different from the liquid receiving position in the state where (i) the at least the first amount of liquid is present in the interior chamber, and (ii) the at least the part of the medical device protrudes into the interior chamber via the second opening and is positioned at the particular location and in the particular configuration in the interior chamber.

In some embodiments, the gas removal apparatus may be further configured such that the second opening is located at least proximate the uppermost surface of the at least the first amount of liquid present in the interior chamber when the gas removal apparatus is arranged in the liquid receiving position in the state where (a) the at least the first amount of liquid is present in the interior chamber, and (b) the at least the part of the medical device protrudes into the interior chamber via the second opening and is positioned at a particular location and in the particular configuration in the interior chamber. In some embodiments, the gas removal apparatus may be operable to laterally drain liquid in the interior chamber through the second opening when the gas removal apparatus is in (c) the liquid receiving position, or (d) the another position different from the liquid receiving position, or in each of (c) and (d).

In some embodiments, the at least the part of the medical device may be selectively movable between a first configuration where the at least the part of the medical device is sized to be deliverable through the second opening, and a second configuration where the at least the part of the medical device is sized too large to be deliverable through the second opening, and wherein the at least the part of the medical device is in the second configuration in the particular configuration in the interior chamber. In some embodiments, the particular configuration in the interior chamber may include a particular orientation of the at least the part of the medical device with respect to the interior chamber.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, each of at least one surface of the one or more first contact surfaces may oppose the filling surface across the interior chamber.

In some embodiments, the filling surface may be an external surface of the gas removal apparatus. In some embodiments, the filling surface may be configured to receive a pouring of the at least the first amount of liquid when the gas removal apparatus is arranged in the liquid receiving position. In some embodiments, the gas removal apparatus may be configured such that, when arranged in the liquid receiving position in a state where the at least the first amount of liquid is present in the interior chamber, the filling surface has a sloped orientation relative to the uppermost surface of the at least the first amount of liquid present in the interior chamber. In some embodiments, the gas removal apparatus may be configured such that in a state where the gas removal apparatus is arranged in the liquid receiving position while supported on a level surface, and where the at least the first amount of liquid is present in the interior chamber, the filling surface has a sloped orientation relative to the uppermost surface of the at least the first amount of liquid present in the interior chamber.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, each of (c) the filling surface and (d) at least one surface of the one or more first contact surfaces may have a sloped orientation relative to each of at least one surface of the one or more second contact surfaces. In some embodiments, (c) the filling surface may be configured to slope toward the one or more first contact surfaces as the filling surface extends upward when the gas removal apparatus is arranged in the another position different from the liquid receiving position, (d) the one or more first contact surfaces may be configured to slope toward the filling surface as the one or more first contact surfaces extend upward when the gas removal apparatus is arranged in the another position different from the liquid receiving position, or both (c) and (d). In some embodiments, the filling surface may be configured to be out of plumb by a first angular amount when the gas removal apparatus is arranged in the liquid receiving position on a level surface, and each of at least one of the one or more first contact surfaces may be out of plumb by a second angular amount when the gas removal apparatus is arranged in the another position different from the liquid receiving position on the level surface. In some embodiments, the first angular amount may be substantially equal to the second angular amount. In some embodiments, the first angular amount may vary by no more than twenty percent of the second angular amount or the second angular amount may vary by no more than twenty percent of the first angular amount. In some embodiments, the filling surface may be configured to be out of level by a first angular amount when the gas removal apparatus is arranged in the liquid receiving position on a level surface, and each of at least one of the one or more second contact surfaces may be configured to be out of plumb by a second angular amount when the gas removal apparatus is arranged in the liquid receiving position on the level surface. In some embodiments, the first angular amount may be different from the second angular amount. In some embodiments, a magnitude of the first angular amount may be greater than a magnitude of the second angular amount. In some embodiments, a magnitude of the first angular amount may be nominally twice the magnitude of the second angular amount.

In some embodiments, the first opening may be an elongated opening. In some embodiments, a shape of the first opening may be different from a shape of the second opening.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, the first opening may be an elongated opening arranged between the end of the filling surface and one or more third surfaces of the gas removal apparatus such that the received at least the first amount of liquid caused to flow along the filling surface enters the interior chamber via the elongated opening. In some embodiments, at least some of the received at least the first amount of liquid caused to flow along the filling surface and enter the interior chamber via the elongated opening may be then caused to flow along at least a portion of at least one third surface of the one or more third surfaces of the gas removal apparatus.

In some embodiments, the filling surface and at least one first contact surface among the one or more first contact surfaces oppose each other for a first distance, and a second distance between the filling surface and the at least one first contact surface may increase as at least part of the first distance is traversed away from the end of the filling surface where the first opening is arranged.

Various apparatuses may be defined by combinations (which includes subcombinations) of the apparatuses described above.

According to some embodiments, a gas removal apparatus is provided. The gas removal apparatus may be configured to receive a first amount of liquid effective to remove gas bubbles from at least a part of a medical device removably disposed in the gas removal apparatus. In some embodiments, the gas removal apparatus may include an interior chamber configured to hold the at least the first amount of liquid. In some embodiments, the gas removal apparatus may include a wall portion including a first surface and a second surface opposite across a thickness of the wall portion from the first surface, the first surface of the wall portion being configured to receive at least the first amount of liquid and cause the received at least the first amount of liquid to flow along the first surface of the wall portion to the interior chamber when the gas removal apparatus is arranged in a liquid receiving position, and the second surface of the wall portion defining at least part of the interior chamber. In some embodiments, at least a portion of the second surface of the wall portion may be configured to, when the gas removal apparatus is arranged in the liquid receiving position in a state where the at least the first amount of liquid is present in the interior chamber, not contact the at least the first amount of liquid present in the interior chamber. In some embodiments, the at least the portion of the second surface of the wall portion may be configured to, when the gas removal apparatus is arranged in another position different from the liquid receiving position in the state where the at least the first amount of liquid is present in the interior chamber, contact the at least the first amount of liquid present in the interior chamber.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, each of at least one surface of the one or more first contact surfaces may oppose the second surface of the wall portion across the interior chamber.

In some embodiments, the first surface of the wall portion may be an external surface of the gas removal apparatus. In some embodiments, the gas removal apparatus may include a first opening arranged at an end of the wall portion and configured to provide a first path into the interior chamber, the first surface of the wall portion configured such that the received at least the first amount of liquid caused to flow along the first surface of the wall portion to the interior chamber when the gas removal apparatus is arranged in the liquid receiving position enters the interior chamber via the first path provided by the first opening. In some embodiments, the gas removal apparatus may include a second opening configured to provide a second path into the interior chamber and configured to receive the medical device such that the at least the part of the medical device enters the interior chamber via the second path provided by the second opening, the first path into the interior chamber and the second path into the interior chamber being mutually exclusive paths into the interior chamber. In some embodiments, the first opening may be an elongated opening. In some embodiments, a shape of the first opening may be different from a shape of the second opening.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, the gas removal apparatus may include a first opening arranged at an end of the wall portion and configured to provide a first path into the interior chamber, the first surface of the wall portion configured such that the received at least the first amount of liquid caused to flow along the first surface of the wall portion to the interior chamber when the gas removal apparatus is arranged in the liquid receiving position enters the interior chamber via the first path provided by the first opening. In some embodiments, the first opening may be an elongated opening arranged between the end of the first surface of the wall portion and one or more third surfaces of the gas removal apparatus such that the liquid flowing along the first surface of the wall portion enters the interior chamber via the elongated opening. In some embodiments, at least some of the received at least the first amount of liquid caused to flow along the first surface of the wall portion and enter the interior chamber via the elongated opening may then be caused to flow along at least a portion of at least one third surface of the one or more third surfaces of the gas removal apparatus. In some embodiments, the first surface of the wall portion, the second surface of the wall portion, or each of both the first surface of the wall portion and the second surface of the wall portion may have a sloped orientation relative to (a) each of at least one of the one or more first contact surfaces, (b) each of at least one of the one or more second contact surfaces, or both (a) and (b).

In some embodiments, the gas removal apparatus may be configured such that, when arranged in the liquid receiving position in the state where the at least the first amount of liquid is present in the interior chamber, the first surface of the wall portion, the second surface of the wall portion, or each of both the first surface of the wall portion and the second surface of the wall portion has a sloped orientation relative to an uppermost surface of the at least the first amount of liquid present in the interior chamber.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, (a) the first surface of the wall portion, the second surface of the wall portion, or each of both the first surface of the wall portion and the second surface of the wall portion may slope toward each of at least one surface of the one or more first contact surfaces as the wall portion extends upward when the gas removal apparatus is arranged in the another position different from the liquid receiving position while supported by the supporting object, (b) each of at least one surface of the one or more first contact surfaces may slope toward the first surface of the wall portion, the second surface of the wall portion, or each of both the first surface of the wall portion and the second surface of the wall portion as the one or more first contact surfaces extend upward when the gas removal apparatus is arranged in the another position different from the liquid receiving position while supported by the supporting object, or both (a) and (b). In some embodiments, another wall portion includes the one or more first contact surfaces and a third surface opposite across a thickness of the another wall portion from the one or more first contact surfaces, the third surface of the another wall portion defining at least part of the interior chamber. In some embodiments, the first surface of the wall portion, the second surface of the wall portion, or each of both the first surface of the wall portion and the second surface of the wall portion may be configured to be out of plumb by a first angular amount when the gas removal apparatus is arranged in the another position different from the liquid receiving position on a level surface, and the third surface of the another wall portion may be configured to be out of plumb by a second angular amount when the gas removal apparatus is arranged in the another position different from the liquid receiving position on the level surface. In some embodiments, the first angular amount may be substantially equal to the second angular amount. In some embodiments, the first angular amount may vary by no more than twenty percent of the second angular amount or the second angular amount varies by no more than twenty percent of the first angular amount.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, another wall portion includes the one or more first contact surfaces and a third surface opposite across a thickness of the another wall portion from the one or more first contact surfaces, the third surface of the another wall portion being opposite across the interior chamber from the second surface of the wall portion. In some embodiments, the first surface of the wall portion, the second surface of the wall portion, or each of both the first surface of the wall portion and the second surface of the wall portion may be configured to be out of plumb by a first angular amount when the gas removal apparatus is arranged in the another position different from the liquid receiving position on a level surface, and the third surface of the another wall portion may be configured to be out of plumb by a second angular amount when the gas removal apparatus is arranged in the another position different from the liquid receiving position on the level surface.

In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, the first surface of the wall portion, the second surface of the wall portion, or each of both the first surface of the wall portion and the second surface of the wall portion may be configured to be out of level by a first angular amount when the gas removal apparatus is in the liquid receiving position on a level surface, and at least one surface of the one or more second contact surfaces may be configured to be out of plumb by a second angular amount when the gas removal apparatus is in the liquid receiving position on the level surface. In some embodiments, the first angular amount may be different from the second angular amount. In some embodiments, a magnitude of the first angular amount may be greater than a magnitude of the second angular amount. In some embodiments, a magnitude of the first angular amount may be nominally twice the magnitude of the second angular amount. In some embodiments, the gas removal apparatus may further include one or more first contact surfaces configured to contact a supporting object when the gas removal apparatus is arranged in the liquid receiving position while supported by the supporting object, and one or more second contact surfaces configured to contact the supporting object when the gas removal apparatus is arranged in the another position different from the liquid receiving position while supported by the supporting object. In some embodiments, the one or more first contact surfaces may be arranged to contact the supporting object at each of a first set of three or more points of contact when the gas removal apparatus is arranged in the liquid receiving position while supported by the supporting object, and at least three points of contact of the first set of three or more points of contact are arranged non-colinearly. In some embodiments, the one or more second contact surfaces may be arranged to contact the supporting object at each of a second set of three or more points of contact when the gas removal apparatus is arranged in the another position different from the liquid receiving position while supported by the supporting object, and at least three points of contact of the second set of three or more points of contact are arranged non-colinearly.

In some embodiments, no portion of the second surface of the wall portion is configured to, when the gas removal apparatus is arranged in the liquid receiving position in a state where the at least the first amount of liquid is present in the interior chamber, contact the at least the first amount of liquid present in the interior chamber. In some embodiments, the second surface of the wall portion and an interior surface opposite across a thickness of the one or more first contact surfaces oppose each other for a first distance, and a second distance between the second surface of the wall portion and the interior surface may increase as at least part of the first distance is traversed away from an opening arranged at an end of the wall portion and configured to provide a first path into the interior chamber.

Various apparatuses may be defined by combinations (which includes subcombinations) of the apparatuses described above.

According to some embodiments, a method for removing gas bubbles from at least a part of a medical device disposed in an interior chamber of a gas removal apparatus may be summarized as including providing a liquid to the interior chamber of the gas removal apparatus while the gas removal apparatus is arranged in a first orientation, the provided liquid entering the interior chamber of the gas removal apparatus via a first opening in the gas removal apparatus. In some embodiments, the method may include moving, after the providing the liquid to the interior chamber of the gas removal apparatus while the gas removal apparatus is arranged in the first orientation, the gas removal apparatus from the first orientation to a second orientation, the second orientation being different from the first orientation. In some embodiments, the method may include moving the at least the part of the medical device disposed in the interior chamber of the gas removal apparatus while the gas removal apparatus is arranged in the second orientation to effect removal of gas bubbles from the at least the part of the medical device due to an interaction between the at least the part of the medical device and the provided liquid present in the interior chamber of the gas removal apparatus. In some embodiments, the method may include moving, after the moving the at least the part of the medical device, the gas removal apparatus from the second orientation to a third orientation, the third orientation different from the second orientation. In some embodiments, the method may include removing the at least the part of the medical device from the interior chamber of the gas removal apparatus, the at least the part of the medical device being removed from the interior chamber of the gas removal apparatus via a second opening in the gas removal apparatus other than the first opening in the gas removal apparatus.

In some embodiments, the removing the at least the part of the medical device from the interior chamber of the gas removal apparatus may include retracting the at least the part of the medical device via the second opening into a fluid vessel physically coupled to the gas removal apparatus. In some embodiments, the method may further include decoupling the fluid vessel from the gas removal apparatus after the retracting the at least the part of the medical device. In some embodiments, retracting the at least the part of the medical device via the second opening into the fluid vessel physically coupled to the gas removal apparatus may occur when the gas removal apparatus is arranged in the second orientation. In some embodiments, the decoupling the fluid vessel from the gas removal apparatus may occur when the gas removal apparatus is arranged in an orientation other than the second orientation. In some embodiments, the decoupling the fluid vessel from the gas removal apparatus may occur after the moving the gas removal apparatus from the second orientation to the third orientation.

In some embodiments, (a) the gas removal apparatus is supported by a first object while arranged in the first orientation, or (b) the gas removal chamber is supported by a second object while arranged in the second orientation, or (c) the gas removal apparatus is supported by a third object while arranged in the third orientation, or (a) and (b), or (a) and (c), or (b) and (c), or (a), (b), and (c). In some embodiments, (d) the first object and the second object may be the same object, or (e) the first object and the third object may be the same object, or (f) the second object and the third object may be the same object, or (g) the first object, the second object and the third object may be the same object. In some embodiments, (d) the gas removal apparatus may be arranged on the first object while arranged in the first orientation, (e) the gas removal apparatus may be arranged on the second object while arranged in the second orientation, or (f) the gas removal apparatus may be arranged on the third object while arranged in the third orientation, or (d) and (e), or (d) and (f), or (e) and (f), or (d), (e), and (f).

In some embodiments, the liquid may be provided to the interior chamber of the gas removal apparatus while the gas removal apparatus is arranged in the first orientation. In some embodiments, the liquid may be provided to the interior chamber of the gas removal apparatus while the at least the part of the medical device is present in the interior chamber.

Various methods may be defined by combinations (which includes subcombinations) of the methods described above.

Various embodiments of the present invention may include systems, devices, or machines that are or include combinations or subsets of any one or more of the systems, devices, or machines and associated features thereof described herein.

Further, all or part of any one or more of the systems, devices, or machines discussed herein or combinations or sub-combinations thereof may implement or execute all or part of any one or more of the processes or methods discussed herein or combinations or sub-combinations thereof.

Further, any of all or part of one or more of the methods or processes and associated features thereof discussed herein may be implemented or executed by all or part of a device system, apparatus, or machine, such as all or a part of any of one or more of the systems, apparatuses, or machines described herein or a combination or sub-combination thereof.

BRIEF DESCRIPTION OF THE DRAWINGS

It is to be understood that the attached drawings are for purposes of illustrating aspects of various embodiments and may include elements that are not to scale.

FIG. 4A is a perspective view of a gas removal apparatus according to some embodiments.

FIG. 4B is another perspective view of a gas removal apparatus according to some embodiments.

FIG. 4C is a side view of a gas removal apparatus positioned in a liquid receiving position according to some embodiments.

FIG. 4D is a side view of a gas removal apparatus positioned in another position different from a liquid receiving position according to some embodiments.

DETAILED DESCRIPTION

Figure 1:
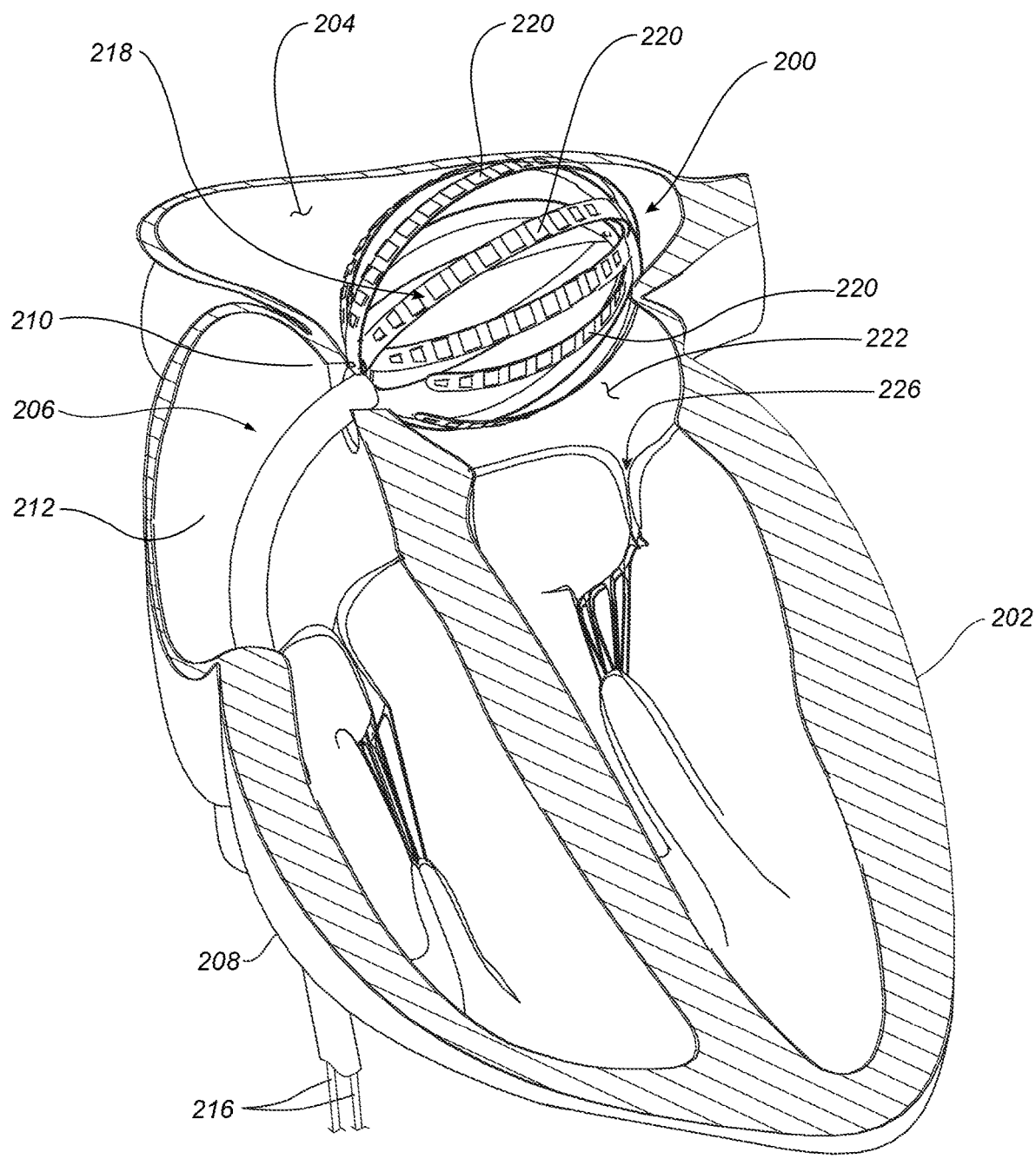
FIG. 1 is a cutaway diagram of a heart showing an example of a medical device therein in a deployed or expanded configuration, the medical device suitable for undergoing flushing of undesired fluid, e.g., air, by various embodiments of one or more of the inventive flushing apparatuses described herein prior to insertion into the heart, according to some embodiments of the present invention.

Various embodiments of the present invention address at least the above-discussed need and provide technical solutions in the art with inventive medical device flushing or gas removal systems and methods. In some embodiments, such systems include an improved structure of an enclosure of a gas removal apparatus, and such methods include inserting at least part of (e.g., a manipulable portion of an elongate shaft member) of a catheter device system into an interior chamber of the gas removal apparatus. In some embodiments, a liquid (e.g., flushing fluid) is provided, via a first opening of the gas removal apparatus, to the interior chamber of the gas removal apparatus while the gas removal apparatus is in a first orientation. In some embodiments, after the liquid is provided to the interior chamber, the gas removal apparatus is moved from the first orientation to a second orientation different from the first orientation. In some embodiments, while the gas removal chamber is in the second orientation, the part of the catheter device system located in the interior chamber is moved to effect removal of gas bubbles from the part of the catheter device system. In some embodiments, after the movement of the part of the catheter device system to effect the removal of gas bubbles therefrom, the gas removal apparatus is moved from the second orientation to a third orientation different from the second orientation. In some embodiments, the part of the catheter device system is removed from the interior chamber of the gas removal apparatus via a second opening of the gas removal apparatus other than the first opening. It should be noted that the invention is not limited to these or any other examples or improvements, which are referred to for purposes of illustration only.

In this regard, in the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase 'based at least on A' includes A as well as the possibility of one or more other additional elements besides A. In the same manner, the phrase 'based on A' includes A, as well as the possibility of one or more other additional elements besides A. However, the phrase 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase 'configured only to A' means a configuration to perform only A.

The word "device", the word "machine", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified, according to various embodiments that a device or machine or device system resides entirely within a same housing to exclude embodiments where the respective device, machine, or device system resides across different housings. The word "device" may equivalently be referred to as a "device system" in some embodiments. Various embodiments described herein refer to the flushing or otherwise removal of unwanted gas bubbles from at least part of a medical device. Such medical devices can include various catheter devices or catheter device systems (e.g., percutaneously or intravascularly deployable catheter devices or device systems). Accordingly, in various embodiments, the phrases "medical device" and "catheter device" may be used interchangeably.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers the event A.

In some embodiments, the term "adjacent", the term "proximate", and the like refer at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", and the like additionally or alternatively refer to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", and the like additionally or alternatively refer to at least a sufficient closeness between the objects defined as adjacent, proximate, and the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", and the like are not limited to any of the above example definitions, according to some embodiments. In addition, the term "adjacent" and the term "proximate" do not have the same definition, according to some embodiments.

The term "proximal", in the context of a proximal portion, proximal location, and the like of a medical device, includes, for example, the portion, location, and the like, being or being configured to be further away from a patient or portion of or region within a patient (e.g., a bodily cavity) intended to be treated or assessed by the medical device, as compared to a distal portion, location, and the like of the medical device, according to some embodiments. In some embodiments, the term "proximal", in the context of a proximal portion, proximal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, after or behind a distal portion, location, and the like of the medical device. On the other hand, the term "distal", in the context of a distal portion, distal location, and the like of a medical device, includes, for example, the portion, location, and the like, being or being configured to be closer to a patient or portion of or region within a patient (e.g., a bodily cavity) intended to be treated or assessed by the medical device, as compared to a proximal portion, location, and the like of the medical device, according to some embodiments. In some embodiments, the term "distal", in the context of a distal portion, distal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, before or ahead of a proximal portion, location, and the like of the medical device.

The word "ablation" as used in this disclosure should be understood to include, for example, any disruption to certain properties of tissue. Most commonly, the disruption is to the electrical conductivity and is achieved by heating, which can be generated with resistive or radio-frequency (RF) techniques for example. However, any other technique for such disruption may be included when the term "ablation" is used, such as mechanical, chemical, electroporation or optical techniques.

The phrase "bodily opening" as used in this disclosure should be understood to include, for example, a naturally occurring bodily opening or channel or lumen; a bodily opening or channel or lumen or perforation formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The phrase "bodily cavity" as used in this disclosure should be understood to mean a cavity in a body. The bodily cavity may be a cavity provided in a bodily organ (e.g., an intra-cardiac cavity or chamber of a heart). The bodily cavity may be provided by a bodily vessel.

The word "tissue" as used in some embodiments in this disclosure should be understood to include, for example, any surface-forming tissue that is used to form a surface of a body or a surface within a bodily cavity, a surface of an anatomical feature or a surface of a feature associated with a bodily opening positioned in fluid communication with the bodily cavity. The tissue can include, for example, part or all of a tissue wall or membrane that defines a surface of the bodily cavity. In this regard, the tissue can form an interior surface of the cavity that surrounds a fluid within the cavity. In the case of cardiac applications, tissue can include, for example, tissue used to form an interior surface of an intra-cardiac cavity such as a left atrium or right atrium. In some embodiments, tissue is non-excised tissue. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include, for example, an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed.

The phrase "physically coupled" is intended to include, in some embodiments, a coupling between two objects that involves a coupling between the two objects where the two objects physically contact each other at least in one state of the coupling between the two objects. The phrases "fixedly coupled", "permanently coupled", and the like, are intended to include, in some embodiments, a secure coupling between two objects that, in some embodiments, does not involve or include a mechanism configured to release the coupling of the two objects. The phrases "removably coupled", "detachably coupled", and the like, are intended to include, in some embodiments, a coupling between two objects that, in some embodiments, allows such coupling to be repeatedly disengaged and re-engaged without damaging the coupling (if a distinct coupling mechanism exists, e.g., in contrast to an interference fit that relies on friction), without damaging either or both of the objects, or without damaging the coupling (if a distinct coupling mechanism exists). The phrase "operatively coupled" is intended to include, for example, a coupling between two objects that transmits force, energy, information, or other influence at least from one of the two objects to the other of the two objects. An operative coupling does not exclude the possibility of a physical or fixed coupling in addition to the operative coupling. Unless otherwise explicitly noted or required by context, for any connection or coupling, direct or indirect, between components, devices, or other physical objects described herein, different embodiments include different ones of the above-described coupling types for such components, devices, or other physical objects. For example, unless otherwise explicitly noted or required by context, if a first physical object is shown in the figures or described in this text as being connected or coupled, directly or indirectly, to a second physical object, some embodiments will have the first physical object fixedly coupled to the second physical object; other embodiments will have the first physical object permanently coupled to the second physical object; other embodiments will have the first physical object removably or detachably coupled to the second physical object; other embodiments will have the first physical object not fixedly or permanently coupled to the second physical object while having the first physical object physically coupled to the second physical object; other embodiments will have the first physical object not physically coupled or fixedly coupled to the second physical object, but will have the first physical object operatively coupled to the second physical object; etc.

The word "fluid", as used in this disclosure, should be understood to include, for example, liquid or gas. In this regard, various embodiments of the present invention are described herein in the context of providing a flushing fluid to flush a medical device of undesired fluid (e.g., air). It is quite common for the flushing fluid to be a liquid such as saline or heparinized saline.

In some embodiments, the phrases "fluid communication", "fluidically communicate", "fluidically coupled", "fluidly communicate", "fluidly coupled", and the like, are intended to include, for example, a port or opening, of a physical object leading to a lumen, chamber, or other internal cavity, where the port, opening, lumen, or internal cavity leads to a body (e.g., a source or drain) of a first fluid, such that (a) at least some of the first fluid moves or is able to move through (1) the port or opening into the lumen, chamber, or other internal cavity, (2) the lumen, chamber, or other internal cavity into the port or opening, or both (a)(1) and (a)(2); (b) at least some of a second fluid moves or is able to move through (1) the lumen, chamber, or other internal cavity into the port or opening, (2) the port or opening into the lumen or other internal cavity, or both (b)(1) and (b)(2); or both (a) and (b). In some embodiments, the first fluid and the second fluid are the same. In some embodiments, the first fluid and the second fluid are different.

Various embodiments of catheter systems or catheter device systems are described herein. It should be noted that any catheter system described herein may also be referred to as a medical system or medical device system. Some of the described devices of such systems are medical devices that are percutaneously or intravascularly deployed. Some of the described devices are deployed through a bodily opening that is accessible without puncturing, cutting or otherwise perforating bodily tissue to create an access to the bodily opening. Some of the described devices employ transducer-based devices or device systems. Some of the described devices are movable between a delivery or unexpanded configuration in which a portion of the device is sized, shaped, or both to be deliverable through a bodily opening leading to a bodily cavity, and an expanded or deployed configuration in which the portion of the device has a size, shape, or both too large to be deliverable through the bodily opening leading to the bodily cavity. An example of an expanded or deployed configuration is when the portion of the catheter system is in a state in which the portion of the catheter system is in its intended operational configuration. In a state in which the portion of the catheter system (e.g., at least the manipulable portion 200 or 300 discussed below) is inside a bodily cavity, the deployed configuration may be an expanded state of the portion of the catheter system in which the portion of the catheter system is configured to interact with tissue within the bodily cavity to perform a medical procedure on a patient. In a state in which the portion of the catheter system (e.g., at least the manipulable portion 200 or 300 discussed below) is not within any part of a patient's body (e.g., during testing of the catheter system, during flushing of the catheter system as discussed below, or some other pre-medical procedure or post-medical procedure state), the deployed configuration may be the expanded state of the portion of the catheter system in which the portion of the catheter system would normally be configured to interact with tissue if within a bodily cavity, but is not configured to interact with tissue since it is not within a bodily cavity. Another example of the expanded or deployed configuration is when the portion of the catheter system is being changed from the delivery configuration to the intended operational state to a point in which the portion of the device now has a size, shape, or both too large to be deliverable through the bodily opening leading to the bodily cavity. In some embodiments, at least a portion of at least one of the described devices has a dimension or size that is smaller in the delivery or unexpanded configuration than a corresponding dimension or size of the at least a portion of at least one of the described devices in the expanded or deployed configuration.

In some example embodiments, the catheter system includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical device system to map the cavity, for example using positions of openings or ports into and out of the cavity to determine a position or orientation (i.e., pose), or both of the portion of the device in the bodily cavity. In some example embodiments, the described devices are capable of ablating tissue in a desired pattern within the bodily cavity. In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing.

FIG. 1 shows a portion of a catheter system, according to some embodiments, such portion including a transducer-based device 200, which may be at least part of a medical device useful in investigating or treating a bodily organ, for example, a heart 202, according to some example embodiments. The transducer-based device 200 may also be referred to as a manipulable portion, due to its ability to have its size, shape, or both size and shape altered, according to some embodiments described below. Transducer-based device 200 can be percutaneously or intravascularly inserted into a portion of the heart 202, such as an intra-cardiac cavity like left atrium 204. The components of the transducer-based device 200 (as well as the transducer-based device 300, and the gas removal apparatus 600, described below) may be sterile.

In the example of FIG. 1, the illustrated portion of the catheter device system also includes a catheter 206, which may be inserted via the inferior vena cava 208 and may penetrate through a bodily opening in transatrial septum 210 from right atrium 212. In other embodiments, other paths may be taken.

Catheter 206 includes an elongate flexible rod or elongate shaft member appropriately sized to be delivered percutaneously or intravascularly. Various portions of catheter 206 may be steerable. Catheter 206 may include one or more lumens, for example within the elongate shaft member. The lumen(s) may carry one or more communications or power paths, or both. For example, the lumens(s) may carry one or more electrical conductors 216 (two shown in this embodiment). Electrical conductors 216 provide electrical connections to transducer-based device 200 that are accessible externally from a patient in which the transducer-based device 200 is inserted. The lumen(s) may carry various control elements (e.g., control lines) operatively coupling one or more actuators to a manipulable portion (e.g., manipulable portion 200).

In various embodiments, transducer-based device, or manipulable portion, 200 includes a frame or structure 218, which assumes an unexpanded configuration to facilitate delivery to left atrium 204. Structure 218 is expanded (i.e., shown in a deployed or expanded configuration in FIG. 1) upon delivery to left atrium 204 to position a plurality of transducers 220 (three called out in FIG. 1) proximate the interior surface formed by tissue 222 of left atrium 204. In this regard, it can be stated that one or more of the transducers 220 are movable with one or more parts of the transducer-based device, or manipulable portion, 200. In some embodiments, at least some of the transducers 220 are used to sense a physical characteristic of a fluid (i.e., blood) or tissue 222, or both, that may be used to determine a position or orientation (i.e., pose), or both, of a portion of transducer-based device 200 within, or with respect to left atrium 204. For example, transducers 220 may be used to determine a location of pulmonary vein ostia (not shown) or a mitral valve 226, or both. In some embodiments, at least some of the transducers 220 may be used to selectively ablate portions of the tissue 222. For example, some of the transducers 220 may be used to ablate a pattern or path around various ones of the bodily openings, ports or pulmonary vein ostia, for instance to reduce or eliminate the occurrence of atrial fibrillation.

Figure 2:
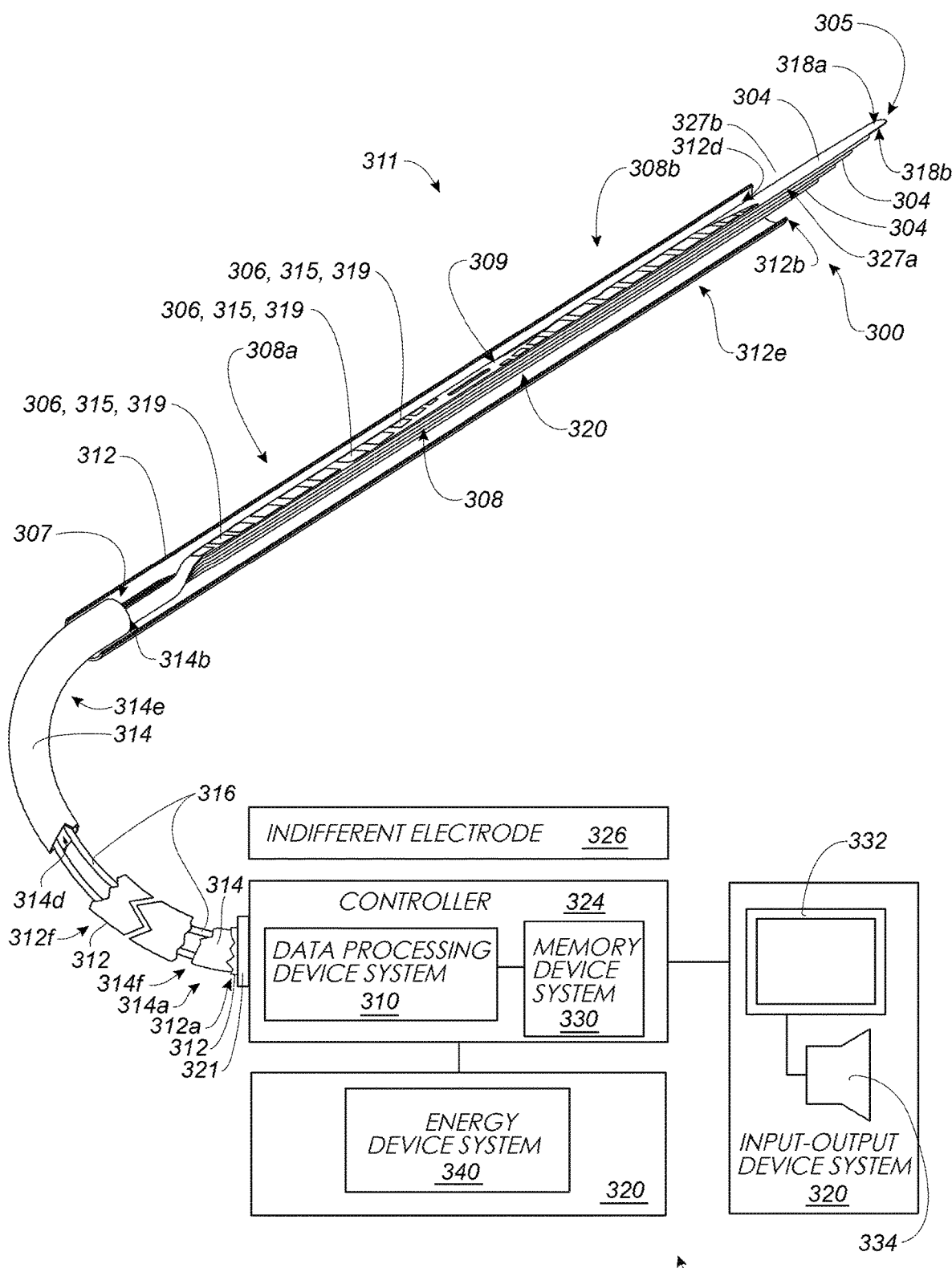
FIG. 2 is a partial schematic view of an example of a medical device, which may represent the medical device shown in FIG. 1, but in a delivery or unexpanded configuration, according to some embodiments.
Figure 3:
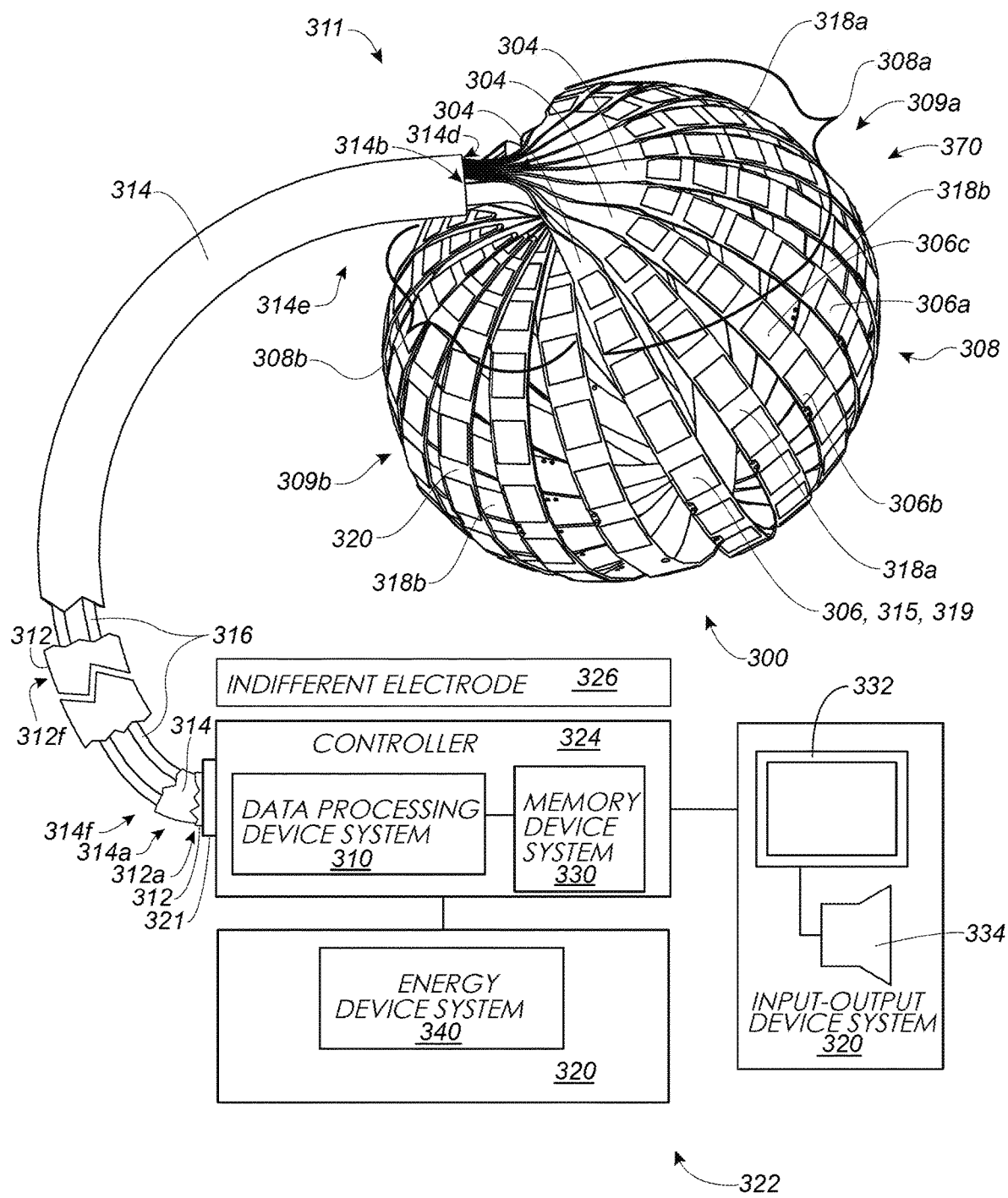
FIG. 3 is a partial schematic view of an example of a medical device, which may represent the medical device shown in FIG. 2, but in a deployed or expanded configuration, according to some embodiments.

FIGS. 2 and 3 show a catheter device system (i.e., a portion thereof shown schematically) that includes a catheter 311, according to some embodiments. The catheter 311 may correspond to catheter 206 and, in this regard, references herein to catheter 311 may be replaced with catheter 206, and vice versa, according to various embodiments. The catheter system of FIGS. 2 and 3 include a transducer-based device (also referred to as a manipulable portion) 300, according to some embodiments. The transducer-based device 300 may correspond to the transducer-based device 200 and, in this regard, may also be referred to as a manipulable portion, due to its ability to have its size, shape, or both size and shape altered, according to some embodiments. In this regard, references herein to transducer-based device 300 may be replaced with transducer-based device 200, and vice versa, according to various embodiments.

The catheter 311 may include an elongate shaft member that includes a proximal end, a distal end, and a length from the proximal end to the distal end. In this regard, the elongate shaft member may form part of or be a catheter sheath, such as catheter sheath 312 including proximal end 312a and distal end 312b. As another example, the elongate shaft member may form part of a catheter, such as elongate shaft member 314 of catheter 311. In various embodiments, the elongate shaft member 314 includes a first lumen 314d. The first lumen 314d may include a first end at least proximate a proximal end 314a of the elongate shaft member 314 and may include a second end at least proximate a distal end 314b of the elongate shaft member 314. Similarly, the catheter sheath 312 may include a first lumen 312d including a first end located at least proximate the proximal end 312a and may include a second end located at least proximate the distal end 312b of elongate shaft member 312. In this regard, various lumens may be provided in elongate shaft member 314, elongate shaft member 312, or both, to provide a passageway for various control leads (e.g., control leads 316) that may extend therethrough to various elongate members 304 or transducers 306 thereof that may form part of manipulable portion 300. Various lumens may be additionally or alternatively provided in elongate shaft member 314, elongate shaft member 312, or both, to provide a passageway for various control lines that may couple an actuator system (e.g., as known in the art, as described, e.g., in U.S. Pat. No. 9,452,016 (Moisa et al.), issued Sep. 27, 2016, which is hereby incorporated herein by reference in its entirety) to the manipulable portion 300 to selectively manipulate the manipulable portion 300 (e.g., selectively manipulating the manipulable portion 300 between an unexpanded or delivery configuration and an expanded or deployed configuration). In various embodiments, the distal end (e.g., 312*b* or 314*b*) of the elongate shaft member is arranged to be deliverable ahead of the proximal end (e.g., 312*a* or 314*a*) of the elongate shaft member through a bodily opening leading to a bodily cavity or a bodily organ. In some embodiments, the manipulable portion 300 is located at the distal end 314*b* of the elongate shaft member 314 or is located closer to the distal end 314*b* of the elongate shaft member 314 than to the proximal end 314*a* of the elongate shaft member 314. In some embodiments, the manipulable portion 300 is not located between the distal end 314*b* of the elongate shaft member 314 and the proximal end 314*a* of the elongate shaft member 314. In some embodiments, the length of the elongate shaft member (e.g., 312 or 314) is sufficient to position the proximal end (e.g., 312*a* or 314*a*) of the elongate shaft member outside a body that includes the bodily cavity during a state in which the distal end (e.g., 312*b* or 314*b*) of the elongate shaft member is positioned in the bodily cavity. In some embodiments, the length of the elongate shaft member (e.g., 312 or 314) is sufficient to position the proximal end (e.g., 312*a* or 314*a*) of the elongate shaft member outside a body that includes the bodily cavity during a state in which the manipulable portion is positioned at a desired location in the bodily cavity.

In some embodiments, transducer-based device 300 may include a plurality of elongate members 304 (three called out in each of FIGS. 2 and 3) and a plurality of transducers 306 (three called out in FIG. 2, and three called out in FIG. 3 as 306*a*, 306*b*, and 306*c*). As will become apparent, the plurality of transducers 306 is positionable within a bodily cavity. For example, in some embodiments, the transducers 306 can be positioned in a bodily cavity by movement into, within, or into and within the bodily cavity, with or without a change in a particular configuration of the plurality of transducers 306. In some embodiments, the plurality of transducers 306 are arrangeable to form a two- or three-dimensional distribution, grid or array of the transducers capable of mapping, ablating, or stimulating an inside surface of a bodily cavity or lumen without requiring mechanical scanning. As shown, for example, in FIG. 2, the plurality of transducers 306 are arranged in a distribution receivable in a bodily cavity, as the transducer-based device 300 and its plurality of transducers 306 are located within the catheter sheath 312 (also referred to as an elongate shaft member). Stated differently, in FIG. 2, for example, the plurality of transducers 306 are arranged in a distribution suitable to be deliverable to a bodily cavity. (It should also be noted, however, that the expanded or deployed configuration (e.g., FIGS. 1 and 3) may also be considered to have the transducers 306 arranged in a distribution receivable in a bodily cavity, as the transducer-based device 300 and its transducers 306 may be returned to the delivery configuration of FIG. 2, for example). In some embodiments, each of the transducers 306 includes an electrode 315 (one called out in FIG. 3) having an energy transmission surface 319 (one called out in FIG. 3) suitable for transmitting energy in various directions. In some embodiments, tissue-ablating energy is transmitted toward or away from an electrode 315. In some embodiments, tissue-based electrophysiological energy is transmitted toward an electrode 315.

The elongate members 304 may form part of a manipulable portion (e.g., 300), and in various embodiments, may form a frame or structure 308, the manipulable portion 300 and frame or structure 308 selectively movable between an unexpanded or delivery configuration (i.e., as shown in FIG. 2) and an expanded or deployed configuration (i.e., as shown in FIG. 3) that may be used to reposition elongate members 304 in a particular desired arrangement. In this regard, it may also be stated that the transducer-based device, or manipulable portion, 300 is selectively movable between an unexpanded or delivery configuration (i.e., as shown in FIG. 2) and an expanded or deployed configuration (i.e., as shown in FIG. 3). In some embodiments, the transducer-based device, or manipulable portion, 300, (e.g., the structure 308 thereof) has a size, shape, or both a size and a shape in the unexpanded or delivery configuration suitable to be percutaneously or intravascularly deliverable through a bodily opening (e.g., via an elongate shaft member such as catheter sheath 312, not shown in FIG. 3) to the bodily cavity. In some embodiments, structure 308 has a size, shape, or both a size and a shape in the expanded or deployed configuration too large to be percutaneously or intravascularly deliverable through a bodily opening (i.e., via catheter sheath 312) to the bodily cavity. The elongate members 304 may form part of a flexible circuit structure (i.e., also known as a flexible printed circuit board (PCB)). The elongate members 304 may include a plurality of different material layers, and each of the elongate members 304 may include a plurality of different material layers. The structure 308 may include a shape memory material, for instance Nitinol. The structure 308 may include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern. The number of elongate members depicted in FIG. 3 is non-limiting. The structure 308 may correspond to structure 218, and, in this regard, references herein to structure 308 may be replaced with structure 218, and vice versa, according to various embodiments.

Referring to FIGS. 2 and 3, transducer-based device or manipulable portion 300 may communicate with, receive power from, or be controlled by a control system 322. In some embodiments, elongate members 304 may form a portion of control leads or electrical conductors 316, for example, by stacking multiple layers, and terminating at a connector 321 or other interface with control system 322. The control leads 316 may correspond to the electrical connectors 216 in FIG. 1 in some embodiments. The control system 322 may include a controller 324 that may include a data processing device system 310 and a memory device system 330 that stores data and instructions that are executable by the data processing device system 310 to process information received from transducer-based device 300 or to control operation of transducer-based device 300, for example, activating various selected transducers 306 to ablate tissue. Controller 324 may include one or more controllers.

In some embodiments, the controller 324 may be configured to control deployment, expansion, retraction, or other manipulations of the shape, positioning, or both shape and positioning of the transducer-based device (e.g., manipulable portion) 300 at least by driving (e.g., by an electric or other motor) movement of various actuators or other catheter system components. In this regard, in some embodiments, the controller 324 is at least part of a control system, which may include one or more actuators, configured to advance at least part of the transducer-based device (e.g., 200 or 300), at least a portion of which may be considered a manipulable portion, out of the catheter sheath 312, retract at least part of the transducer-based device back into the catheter sheath 312, expand, contract, or otherwise change at least part of the shape of the transducer-based device.

Control system 322 may include an input-output device system 320 communicatively connected to the data processing device system 310 (i.e., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other devices to transfer information to, from, or both to and from a user, for example a care provider such as a health care provider or technician. For example, output from a mapping process may be displayed on a display device system 332.

Control system 322 may also include an energy device system 340 including one or more energy devices connected to transducers 306. In this regard, although FIG. 2 shows a communicative connection between the energy device system 340 and the controller 324 (and its data processing device system 310), the energy device system 340 may also be connected to the transducers 306 via a communicative connection that is independent of the communicative connection with the controller 324 (and its data processing device system 310). For example, the energy device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through elongate shaft member 314, control leads 316 or catheter sheath 312) that does not pass through the controller 324. In this regard, the energy device system 340 may provide results of its delivering energy to, receiving energy from, or both delivering energy to and receiving energy from one or more of the transducers 306 to the controller 324 (and its data processing device system 310) via the communicative connection between the energy device system 340 and the controller 324.

The energy device system 340 may, for example, be connected to various selected transducers 306 to selectively provide energy in the form of electrical current or power (e.g., RF energy), light or low temperature fluid to the various selected transducers 306 to cause ablation of tissue. The energy device system 340 may, for example, selectively provide energy in the form of electrical current to various selected transducers 306 and measure a temperature characteristic, an electrical characteristic, or both at a respective location at least proximate each of the various transducers 306. The energy device system 340 may include as its energy devices various electrical current sources or electrical power sources. In some embodiments, an indifferent electrode 326 is provided to receive at least a portion of the energy transmitted by at least some of the transducers 306. Consequently, although not shown in FIG. 2, the indifferent electrode 326 may be communicatively connected to the energy device system 340 via one or more communication lines in some embodiments. In addition, although shown separately in FIG. 2, indifferent electrode 326 may be considered part of the energy device system 340 in some embodiments. In some embodiments, the indifferent electrode 326 is provided outside the body or at least the bodily cavity in which the transducer-based device (e.g., 200 or 300) or catheter system is, at least in part, located.

In some embodiments, the energy device system 340 may include one or more driving motors configured to drive movement, in response to instructions from the controller 324, of various actuators or other catheter system components to control deployment, expansion, retraction, or other manipulations of the shape, positioning, or both shape and positioning of the transducer-based device (e.g., manipulable portion) 300.

It is understood that input-output device system 320 may include other systems. In some embodiments, input-output device system 320 may optionally include energy device system 340, transducer-based device 300 or both energy device system 340 and transducer-based device 300 by way of non-limiting example.

Structure 308 of transducer-based device 300 may be delivered and retrieved through at least a portion of a catheter member, for example, a catheter sheath 312. In some embodiments, the structure 308 provides expansion and contraction capabilities for a portion of a medical device (e.g., an arrangement, distribution or array of transducers 306). The transducers 306 may form part of, be positioned or located on, affixed to, mounted or otherwise carried on the structure, and the structure may be configurable to be appropriately sized to slide within a lumen of catheter sheath 312 in order to be deployed percutaneously or intravascularly. FIG. 2 shows one embodiment of such a structure.

In some embodiments, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In various embodiments, the intermediate portion 309 of each of the elongate members 304 includes a respective pair of side edges of the front surface 318a, the back surface 318b, or both the front surface 318a and the back surface 318b, the side edges of each pair of side edges opposite to one another, the side edges of each pair of side edges extending between the proximal end 307 and the distal end 305 of the respective elongate member 304. In some embodiments, each pair of side edges includes a first side edge 327a (only one called out in FIG. 2) and a second side edge 327b (only one called out in FIG. 2). In some embodiments, each of the elongate members 304, including each respective intermediate portion 309, is arranged front surface 318a-toward-back surface 318b in a stacked array during an unexpanded or delivery configuration (e.g., FIG. 2). In many cases, a stacked array allows the structure 308 to have a suitable size to be percutaneously or intravascularly deliverable. A stacked array can allow structure 308 to have a spatially efficient size for delivery through a lumen of catheter sheath 312. In some embodiments, the elongate members 304 are arranged to be introduced into a bodily cavity distal end 305 first. For clarity, not all of the elongate members 304 of structure 308 are shown in FIG. 2. A flexible catheter body or elongate shaft member 314 is used to deliver structure 308 through catheter sheath 312. In some embodiments, each elongate member includes a twisted portion proximate proximal end 307.

In some embodiments, each of the elongate members 304 is arranged in a fanned arrangement 370 in FIG. 3. In some embodiments, the fanned arrangement 370 is formed during the expanded or deployed configuration in which the transducer-based device (e.g., manipulable portion) 300 or structure 308 thereof is manipulated to have a size, shape, or both size and shape larger than in the delivery configuration, for example a size, shape, or both size and shape too large for percutaneous or intravascular delivery toward a bodily cavity, or a size, shape, or both size and shape too large for percutaneous or intravascular delivery away from a bodily cavity. In some embodiments, the fanned arrangement 370 is formed during the expanded or deployed configuration in which the transducer-based device (e.g., manipulable portion) 300 or structure 308 thereof is manipulated to have a size, shape, or both size and shape too large to be deliverable through a lumen of catheter sheath 312, for example, a size, shape, or both size and shape too large to be deliverable through a lumen of catheter sheath 312 toward a bodily cavity, or a size, shape, or both size and shape too large to be deliverable through a lumen of catheter sheath 312 away from a bodily cavity.

In some embodiments, the transducer-based device (e.g., manipulable portion) 300 or structure 308 thereof includes a proximal portion 308a having a first domed shape 309a and a distal portion 308b having a second domed shape 309b when the transducer-based device (e.g., manipulable portion) 300 or structure 308 thereof is in the expanded or deployed configuration. In some embodiments, the proximal and the distal portions 308a and 308b include respective portions of elongate members 304. In some embodiments, the transducer-based device (e.g., manipulable portion) 300 or structure 308 thereof is arranged to be delivered or advanced distal portion 308b first (e.g., distal portion 308b ahead of proximal portion 308a) into a bodily cavity when the transducer-based device (e.g., manipulable portion) 300 or structure 308 thereof is in the unexpanded or delivery configuration as shown in FIG. 2. In various example embodiments, each of the front surfaces 318a (two called out in FIG. 3) of the intermediate portions 309 of the plurality of elongate members 304 face outwardly from the structure 308 when the structure 308 is in the deployed configuration. In various example embodiments, each of the front surfaces 318a of the intermediate portions 309 of the plurality of elongate members 304 are positionable to face an interior tissue surface of a bodily cavity in a state in which the structure 308 (i.e., in the deployed configuration) is located in the bodily cavity. In various example embodiments, each of the back surfaces 318b (two called out in FIG. 3) of the intermediate portions 309 of the plurality of elongate members 304 face inwardly toward an interior of the structure 308 when the structure 308 is in the deployed configuration.

The transducers 306 may be arranged in various distributions or arrangements in various embodiments. In some embodiments, various ones of the transducers 306 are spaced apart from one another in a spaced-apart distribution in the delivery configuration shown in FIG. 2. In some embodiments, various ones of the transducers 306 are arranged in a spaced-apart distribution in the deployed configuration shown in FIG. 3. In some embodiments, various pairs of transducers 306 are spaced apart with respect to one another. In other example embodiments, other structures may be employed to support or carry transducers of a transducer-based device such as a transducer-based catheter device. For example, an elongated catheter member may be used to distribute the transducers in a linear or curvilinear array. Basket catheters or balloon catheters may be used to distribute the transducers in a two-dimensional or three-dimensional array.

In some embodiments, a manipulable portion, such as, but not limited to, a transducer-based device (e.g., 200 or 300), is manipulated to transition between an unexpanded or delivery configuration (e.g., FIG. 2) and an expanded or deployed configuration (e.g., FIG. 3) manually (e.g., by a user's manual operation) or at least in part by way of motor-based driving (e.g., from the energy device system 340) of one or more actuators. Motor-based driving may augment or otherwise be in response to manual actions, may be responsive to automated control of a data processing device system (e.g., 310 in FIGS. 2 and 3), or may use a hybrid manual-automated approach.

FIGS. 4A-4J (collectively referred to as FIG. 4) illustrate various aspects of medical device flushing or gas removal apparatuses 600 employed to flush at least a portion of a medical device. In some embodiments, the medical device is a catheter, such as catheter 206 or 311, and the portion of the medical device is at least the manipulable portion 200 or 300 or respective structure 218 or 308 thereof, according to some embodiments.

According to various embodiments associated with at least FIGS. 4A and 4B, gas removal apparatus 600 is provided, the gas removal apparatus 600 being configured according to various embodiments to receive a first amount of liquid effective to remove gas bubbles from at least part of a medical device removably disposed in the gas removal apparatus 600. In some embodiments, the first amount of liquid effective to remove gas bubbles from at least part of a medical device removably disposed in the gas removal apparatus 600 includes an amount of liquid that allows for the at least part of the medical device to be totally submerged in the liquid present in the gas removal apparatus 600 when the gas removal apparatus 600 is arranged in an appropriate position and/or orientation. According to various embodiments, the gas removal apparatus 600 may include an improved vessel or enclosure 602 that includes an interior surface 602a defining at least part of a flushing chamber including a flushing or interior chamber 603 (e.g., seen in FIG. 4C described below) configured to hold at least the first amount of liquid. According to some embodiments, the interior chamber 603 is configured to receive a structure (e.g., at least manipulable portion 300 or structure 308 thereof) of a medical device. According to various embodiments, the structure is a distal end structure of the medical device. For example, manipulable portion 300 or structure 308 may be considered distal end structures of catheter 311, because they are arranged or located on a distal portion (e.g., a distal portion 314e of the elongate shaft member 314 or a distal end portion 312e of the sheath 312) of the catheter 311, which is configured or arranged for insertion into a body of a patient, as opposed to a proximal portion (e.g., a proximal portion 314f of the elongate shaft member 314 or a proximal portion 312f of the sheath 312) of the catheter 311, which is configured or arranged to remain outside the body at least during a state in which the distal portion of the catheter 311 has been positioned at a desired location within the body.

In some embodiments, the manipulable portion 300 or structure 308 of the medical device is not configured to operate on or interact with tissue of a bodily cavity in a state in which the manipulable portion 300 or structure 308 is located within the enclosure 602 or any part of the gas removal apparatus 600. In other words, the manipulable portion 300 or structure 308 is configured to operate on or interact with tissue of a bodily cavity in a state in which the manipulable portion 300 or structure 308 is not located within any part of the gas removal apparatus 600 including the enclosure 602. For example, the elongate members 304 may include transducers, such as transducers 306 or transducers 220, which are configured to operate on or interact with tissue of a bodily cavity in a state in which the manipulable portion 300 or structure 308 is not located within any part of the gas removal apparatus 600 including the enclosure 602 or interior chamber 603. In a state in which the manipulable portion 300 or structure 308 is located within a part of the gas removal apparatus 600, such as the enclosure 602 or interior chamber 603, at least the part of the gas removal apparatus 600 would prevent the transducers' operation on or interaction with tissue of a bodily cavity, according to various embodiments. In various embodiments, enclosure 602 is configured to not be deliverable, or configured to be incapable of being delivered, through the same bodily opening (e.g., via a percutaneous or intravascular delivery) that an elongate shaft member (e.g., 312 or 314) of the medical device system (or catheter device system) is configured to be deliverable through. In other words, there is no state of the enclosure 602 in which it is configured to be deliverable through the same bodily opening (e.g., via a percutaneous or intravascular delivery) that an elongate shaft member (e.g., 312 or 314) of the medical device system (or catheter device system) is configured to be deliverable through. For example, the enclosure 602 may include a size (e.g., an overall size or dimension) that is too large or renders the enclosure 602 too large for delivery of the enclosure 602 through the bodily opening leading to a bodily cavity to which the elongate shaft member (312 or 314) is to be delivered. For example, in FIGS. 4F, 4G, and 4H (described in further detail below), enclosure 602 is sized much larger than a size of the structure-receiving opening (e.g., provided by second opening 614 further described below), which is sized, according to various embodiments, to allow for a sliding fit with the at least part of the distal end portion (e.g., 312e or 314e) of the elongate shaft member (e.g., 312 or 314). Accordingly, the size of the structure-receiving opening may approximate the size (e.g., at least be smaller than the size) of the bodily opening through which the elongate shaft member (312 or 314) is to be delivered. Consequently, the enclosure 602 may be physically incapable of being delivered through such a bodily opening because its size is much larger than that of the structure-receiving opening.

In some embodiments, enclosure 602 may be incapable of being deliverable through the bodily opening in various states. For example, in some embodiments, the enclosure 602 may include a size (e.g., an overall size or dimension) that is too large or renders the enclosure 602 too large for delivery of the enclosure 602 through the bodily opening leading to a bodily cavity to which the elongate shaft member (e.g., 312 or 314) is to be delivered at least in a state in which a particular portion or the entirety of the internal chamber 603 is void of a particular liquid (e.g., a liquid such as a flushing liquid such as saline or heparinized saline). In some embodiments, the enclosure 602 may include a size (e.g., an overall size or dimension) that is too large or renders the enclosure 602 too large for delivery of the enclosure 602 through the bodily opening at least in a state in which a particular portion or the entirety of the interior chamber 603 is void of any particular liquid (e.g., void of any liquid whatsoever). In some embodiments, the enclosure 602 may include a size (e.g., an overall size or dimension) that is too large or renders the enclosure 602 too large for delivery of the enclosure 602 through the bodily opening at least in a state in which a portion of the interior chamber 603 in filled with a particular liquid and another portion of the interior chamber 603 is not filled with the particular liquid. Similarly, in some embodiments, the enclosure 602 may include a size (e.g., an overall size or dimension) that is too large or renders the enclosure 602 too large to fit in the bodily cavity to which the elongate shaft member (312 or 314) is to be delivered at least in each of one or more or all of the above-described states. For example, the enclosure 602 may have the above-described size(s) at least in embodiments where the enclosure 602 is formed of a rigid or substantially rigid structure that may be incapable of fitting into the bodily cavity or delivery though the bodily opening leading to the bodily cavity regardless of whether the enclosure 602 is empty of liquid or filled at least in part with liquid. FIGS. 4A and 4B illustrate the enclosure 602 having such a rigid or substantially rigid structure. In some embodiments, enclosure 602 may include a structure that is incapable of collapsing to a size suitable for delivery through the bodily opening leading to the bodily cavity. For example, enclosure 602 may include a flexible structure that is collapsible or compressible to a minimum size that is incapable of allowing delivery of the enclosure 602 through the bodily opening leading to the bodily cavity.

Even if enclosure 602 is a flexible or substantially compliant structure that may allow sufficient compression to possibly fit through the bodily opening, the mere presence of the enclosure 602 during the delivery of the elongate shaft member (e.g., 312 or 314) through the bodily opening may impede, restrict, or prevent a required functioning of the elongate shaft member or catheter that comprises the elongate shaft member. For example, if the elongate shaft member is part of a catheter sheath (e.g., elongate shaft member 312), a delivery of an assembly including the elongate shaft member and enclosure 602 (i.e., positioned over the distal end portion (e.g., 312e) of the elongate shaft member) through the bodily opening would likely position the enclosure 602 so as to impede a subsequent delivery of the catheter or other medical instrument through a lumen of the elongate shaft member. If the elongate shaft member is part of a catheter (e.g., elongate shaft member 314), a delivery of an assembly including the elongate shaft member and enclosure 602 (i.e., positioned over the distal end portion (e.g., 314e) of the elongate shaft member) through the bodily opening would likely position the enclosure 602 so as to impede a subsequent operation of manipulable portion 300 with respect to tissue within the bodily cavity (e.g., tissue ablation or the sensing of various physiological parameters such as tissue electrical potential). In this regard, when the gas removal apparatus 600 is employed, the at least part of the distal end portion (e.g., 312e or 314e) of the elongate shaft member (e.g., 312 or 314) inserted into the enclosure 602 is removed from the interior chamber 603 prior to a delivery of at least the distal end portion (e.g., 312e or 314e) of the elongate shaft member (e.g., 312 or 314) through the bodily opening leading to the bodily cavity, according to some embodiments.

According to some embodiments, the gas removal apparatus 600 may be configured to provide one or additional functions other than removing gas from at least part of a medical device (e.g., manipulable portion 300 or structure 308 described above). For example, in some embodiments, the gas removal apparatus 600 may be employed to protect the at least the part of the medical device (e.g., manipulable portion 300 or structure 308) during various functions such as, but not limited to, packaging of the medical device, transportation or shipping of the medical device, or storage of the medical device prior to use. In some embodiments, the medical device and the gas removal apparatus 600 may be packaged in a container such the at least the part of the medical device (e.g., manipulable portion 300 or structure 308) is provided in a portion (e.g., interior chamber 603) of the gas removal apparatus 600. This arrangement may be motivated for various reasons. For example, providing the at least the part of the medical device (e.g., manipulable portion 300 or structure 308) already in the gas removal apparatus 600 removes an additional step required by medical personnel during the performance of a procedure involving the medical device. In this regard, a flushing procedure of the at least the part of the medical device (e.g., manipulable portion 300 or structure 308) may commence without delay according to some embodiments. By way of another example, providing a package in which the at least the part of the medical device (e.g., manipulable portion 300 or structure 308) is already in the gas removal apparatus 600 may help protect the at least the part of the medical device during transportation or other handling. According to various embodiments, the geometry of various device-containing portions (e.g., interior chamber 603) of the gas removal apparatus 600 may be configured to avoid contact with the at least the portion of the medical device (e.g., manipulable portion 300 or structure 308). A lack of contact may be employed to reduce possible damage to various components such as transducers 306. According to various embodiments, the at least the portion of the medical device (e.g., manipulable portion 300) may assume a delivery configuration (e.g., FIG. 2) when provided in the gas removal apparatus 600. In some embodiments, the at least the portion of the medical device (e.g., manipulable portion 300 or structure 308) may assume an expanded or deployed configuration (e.g., FIG. 3) when provided in the gas removal apparatus 600. It is noted however, that in other embodiments, the medical device and the gas removal apparatus may not be provided to a user as an assemblage, but rather as separate entities that require further user action to insert the at least the portion of the medical device (e.g., manipulable portion 300 or structure 308) into the gas removal apparatus 600.

According to various embodiments, the gas removal apparatus 600 may include a filling surface 605 (e.g., FIG. 4A) configured to receive at least the first amount of liquid and cause the received at least the first amount of liquid to flow along the filling surface 605 to the interior chamber 603 when the gas removal apparatus 600 is arranged in a liquid receiving position 616. For example, FIG. 4C is a side view of enclosure 602 positioned in a liquid receiving position 616 according to some embodiments. The liquid receiving position exemplified in FIG. 4C may be oriented with respect to arrow 606 which is provided to indicate a vertically upward reference direction. The liquid receiving position exemplified in FIG. 4C may, according to some embodiments, correspond to a positioning of the gas removal apparatus 600 on a level surface. The at least the first amount liquid is indicated as 601 in FIG. 4C and includes an uppermost surface 601a, which under the influence of gravity also provides an orientation indicator associated with the liquid receiving position 616 exemplified in FIG. 4C. It is noted that in other embodiments, the gas removal apparatus 600 may be positioned with other orientations according to other possible liquid receiving positions. It is also noted that the liquid receiving position of the gas removal apparatus 600 includes any and all positions or orientations of the gas removal apparatus 600 that allow the filling surface 605 to receive the at least the first amount of liquid 601 and cause the received at least the first amount of liquid 601 to flow along the filling surface 605 to the interior chamber 603. The embodiment of FIG. 4C depicts the gas removal apparatus 600 in liquid receiving position 616, which is merely one example of a position or orientation of the gas removal apparatus 600 that allows the filling surface 605 to receive the at least the first amount of liquid 601 and cause the received at least the first amount of liquid 601 to flow along the filling surface 605 to the interior chamber 603.

According to some embodiments, a first opening 607 may be arranged at an end of the filling surface 605, the first opening 607 configured to provide a first path (exemplified in FIG. 4C by 608) into the interior chamber 603. According to some embodiments, the filling surface 605 may be configured such that the received at least the first amount of the liquid 601 that is caused to flow along the filling surface 605 to the interior chamber 603 when the gas removal apparatus 600 is arranged in the liquid receiving position 616 enters the interior chamber 603 via the first path 608 provided by the first opening 607. The at least the first amount of liquid 601 may be received in various manners by the filling surface 605 according to various embodiments. For example, according to some embodiments, the filling surface 605 may be configured to receive a pouring of the at least the first amount of liquid 601 when the gas removal apparatus 600 is arranged in the liquid receiving position 616. In some embodiments, the at least the first amount of liquid 601 is provided in a supply container or vessel (not shown). Typically, the interior of the supply vessel and its contents (e.g., the at least the first amount of liquid 601) are sterile, while exterior portions of the supply vessel are not. It is typically desired, according to various embodiments, that the at least the first amount of liquid 601 be transferred from the supply container to the gas removal apparatus 600 with little to no contact between the supply container and the gas removal apparatus 600 to avoid contaminating the gas removal apparatus 600 or the at least the first amount of liquid 601. Pouring of the at least the first amount of liquid 601 from the supply container into the gas removal apparatus 600 with no contact between the supply container and the gas removal apparatus 600 may be employed according to some embodiments to reduce possible contamination of the gas removal apparatus 600 and/or the at least the first amount of liquid 601.

In various embodiments, the filling surface 605 is an external surface of the gas removal apparatus 600. In various embodiments, the filling surface 605 may be configured to receive a pouring (e.g., exemplified by arrow "P" indicating an example of a path of liquid being poured onto the filling surface 605) of the at least the first amount of liquid 601 when the gas removal apparatus 600 is arranged in the liquid receiving position 616. In some embodiments, the filling surface 605 is an external surface configured to receive a pouring of the at least the first amount of liquid 601 when the gas removal apparatus 600 is arranged in the liquid receiving position 616 (FIG. 4C). According to various embodiments, it is desired that any pouring of the at least the first amount of liquid 601 occurs while there is a sufficient distance between the supply container and the gas removal apparatus 600 so as to not compromise the sterility of a sterile field surrounding the gas removal apparatus 600. For example, arrow "P" indicates an example of a path of liquid being poured onto the filling surface 605 according to an embodiment where the pouring of the at least the first amount of liquid 601 occurs without compromising the sterility of a sterile field surrounding the gas removal apparatus 600. To facilitate pouring from a "sufficient distance," a relatively large filling surface 605 may be employed according to various embodiments, to facilitate capturing as much of the poured liquid while reducing occurrences of spillage. In this regard, a relatively large filling surface 605 may be "easier to hit or target" during the pouring. For example, the present inventors have employed filling surfaces with dimensions of approximately 107 mm×113 mm according to some embodiments.

According to various embodiments, the filling surface 605 assumes a sloped orientation when the gas removal apparatus 600 is in the liquid receiving position 616 to assist or guide the at least the first amount of liquid 601 into the first opening 607. According to some embodiments, the gas removal apparatus 600 may be configured such that, when arranged in the liquid receiving position 616 in a state where at least the first amount of the liquid 601 is present in the interior chamber 603, the filling surface 605 has a sloped orientation relative to the uppermost surface 601a of the at least the first amount of liquid 601 present in the interior chamber 603. According to various embodiments, the first opening 607 may be located at an end of the filling surface 605 (or in some embodiments may be defined at least in part by an edge of the filling surface 605). In some embodiments, the first opening 607 may be an elongated opening. In some embodiments, the first opening 607 may be an elongated opening arranged between the end of the filling surface 605 and one or more third surfaces 610 of the gas removal apparatus 600 such that the received at least the first amount of liquid 601 caused to flow along the filling surface 605 enters the interior chamber 603 via the elongated opening.

According to various embodiments, a relatively gentle introduction of the at least first amount of liquid 601 into the interior chamber 603 may be desired. For example, when the at least the part of the medical device (e.g., manipulable portion 300) is in the interior chamber 603 during the introduction of the at least the first amount of the liquid 601 into the interior chamber 603, a gentle introduction with reduced levels of agitation or turbulence may be employed to reduce generation of additional or excess gas bubbles on the at least the part of the medical device (e.g., manipulable portion 300 or structure 308) that may arise from the liquid introduction. Various embodiments of the gas removal apparatus 600 may be employed to reduce undesired turbulence during the introduction of at least the first amount of the liquid 601 into the interior chamber 603. In some embodiments, at least some of the first amount of liquid 601 caused to flow along the filling surface 605 and enter the interior chamber 603 via the first opening 607 is then caused to flow along at least a portion of at least one third surface 610 of the one or more third surfaces 610 of the gas removal apparatus 600. In some embodiments, the first opening 607 may be located away from the at least part of the medical device (e.g., manipulable portion 300 or structure 308) located in the interior chamber 603. In some embodiments, the first opening 607 may be located away from the at least part of the medical device (e.g., manipulable portion 300 or structure 308) located in the interior chamber 603 such that the first amount of liquid 601 caused to flow along the filling surface 605 and enter the interior chamber 603 via the first opening 607 does not come into contact with the at least part of the medical device without interacting with one or more surfaces (e.g., one or more third surfaces 610) of the gas removal apparatus 600 first, thereby reducing the velocity of the liquid and softening or dampening the introduction of the at least the first amount of the liquid 601 into the interior chamber 603 (for example, as exemplified in FIG. 4C). In various embodiments in which the first opening 607 is elongated in shape, the elongated first opening 607 may span a width (e.g., a dimension transverse a direction of liquid flow along the filling surface 605) of the filling surface 605 (for example as exemplified in FIG. 4A). This arrangement may be motivated to avoid impeding the flow of the at least the first amount of fluid 601 into interior chamber 603.

According to some embodiments, the gas removal apparatus 600 includes a second opening 614 configured to provide a second path (exemplified by arrow 615 in FIGS. 4A, 4B) into the interior chamber 603 and configured to receive the medical device such the at least part of the medical device (e.g., manipulable portion 300 or structure 308) enters the interior chamber 603 via the second path provided by the second opening 614. According to various embodiments, the first path (e.g., exemplified by arrow 608) into the interior chamber 603 and the second path (e.g., exemplified by arrow 615) into the interior chamber 603 are mutually exclusive paths into the interior chamber 603.

According to various embodiments, the gas removal apparatus 600 may be configured such that, when arranged in the liquid receiving position 616 in a state where (a) the at least the first amount of liquid 601 is present in the interior chamber 603, and (b) the at least part of the medical device (e.g., manipulable portion 300 or structure 308) protrudes into the interior chamber 603 via the second opening 614 and is positioned at a particular location 617 and in a particular configuration in the interior chamber 603, at least a portion of the at least part of the medical device (e.g., manipulable portion 300 or structure 308) is disposed above an uppermost surface 601a of the at least the first amount of liquid 601 present in the interior chamber 603 (for example, as exemplified in FIG. 4C).

According to various embodiments, the gas removal apparatus 600 may be configured such that, when arranged in another position 618 (e.g., FIG. 4D) different from the liquid receiving position 616 in a state where (i) the at least the first amount of liquid 601 is present in the interior chamber 603 and (ii) the at least part of the medical device (e.g., manipulable portion 300 or structure 308) protrudes into the interior chamber 603 via the second opening 614 and is positioned at the particular location 617 and in a particular configuration in the interior chamber 603, the entirety of the at least the part of the medical device (e.g., manipulable portion 300 or structure 308) is disposed below an uppermost surface 601b of the at least the first amount of liquid 601 present in the interior chamber 603.

According to some embodiments, the gas removal apparatus 600 may be moved from the liquid receiving position 616 to the another position 618 different from the liquid receiving position 616 by various manipulations of the gas removal apparatus 600. For example, with reference to FIGS. 4C and 4D, the gas removal apparatus 600 may be moved from the liquid receiving position 616 (FIG. 4C) to the another position 618 (FIG. 4D) by a manipulation that includes a rotation such as that represented by arrow 620 in FIG. 4C. The another position 618 may be different in various manners from the liquid receiving position 616. For example, in FIG. 4D, the another position 618 orients the filling surface 605 in a manner that any liquid received (for example, by pouring) by the filling surface 605 would not flow along the filling surface 605 toward the first opening 607 and into the interior chamber 603 as per some embodiments. Accordingly, in some embodiments, the filling surface 605 is configured to not receive the at least the first amount of liquid 601 and cause the at least the first amount of liquid 601 to flow along the filling surface 605 into the interior chamber 603 when the gas removal apparatus 600 is in the another position 618 different from the liquid receiving position 616. Other reasons may motivate the use of the another position 618 which is different from the liquid receiving position 616. For example, it is desirable that the at least the part of the medical device (e.g., manipulable portion 300 or structure 308) be totally submerged in the first amount of liquid 601 present in the interior chamber 603 during removal of gas bubbles as described in further detail below. Total submersion in the first amount of liquid 601 present in the interior chamber 603 may be desired to avoid exposing the at least the part of the medical device (e.g., manipulable portion 300 or structure 308) to air during a gas removal procedure. FIG. 4D shows a possible positioning of the gas removal apparatus 600 in which the at least the first part of the medical device (e.g., manipulable portion 300 or structure 308) is totally submerged in a manner that would be favorable for gas bubble removal according to some embodiments. Total submergence of the at least the first part of the medical device limits exposure of the at least the first part of the medical device to any air present in the gas removal apparatus 600. FIG. 4C shows a possible positioning of the gas removal apparatus 600 which includes a suitable positioning of a wall portion providing the filling surface 605 to receive the at least the first amount of liquid 601, but which is a particular positioning in which the at least the first part of the medical device (e.g., manipulable portion 300 or structure 308) is not totally submerged in a manner that would be favorable for gas bubble removal according to some embodiments. It is noted that the another position of the gas removal apparatus 600 includes any and all positions or orientations of the gas removal apparatus 600 that allow for, in a state where (i) the at least the first amount of liquid 601 is present in the interior chamber 603, and (ii) the at least the part of the medical device protrudes into the interior chamber 603 via the second opening 614 and is positioned at the particular location and in the particular configuration in the interior chamber 603, the entirety of the at least the part of the medical device to be disposed below an uppermost surface 601b of the at least the first amount of liquid 601 present in the interior chamber 603. The embodiment of FIG. 4D depicts the gas removal apparatus 600 in the another position 618, which is merely one example of a position or orientation of the gas removal apparatus 600 that allows for, in a state where (i) the at least the first amount of liquid 601 is present in the interior chamber 603, and (ii) the at least the part of the medical device protrudes into the interior chamber 603 via the second opening 614 and is positioned at the particular location and in the particular configuration in the interior chamber 603, the entirety of the at least the part of the medical device to be disposed below an uppermost surface 601b of the at least the first amount of liquid 601 present in the interior chamber 603.

According to various embodiments, the at least the first part of the medical device (e.g., manipulable portion 300 or structure 308) is removed from the gas removal apparatus 600 after the gas removal procedure has been completed. In some cases, the second opening 614 may act as a fluid drain after the at least the first part of the medical device (e.g., manipulable portion 300 or structure 308) is removed from the gas removal apparatus 600. If the gas removal apparatus 600 were in the another position 618 (e.g., FIG. 4D) after removal of the at least the first part of the medical device (e.g., manipulable portion 300 or structure 308) from the gas removal apparatus 600, second opening 614 would be submerged in the at least first amount of liquid 601 present in the interior chamber 603. If the second opening 614 were to act as a fluid drain when the gas removal apparatus 600 was in the another position 618, then a relatively large amount of the liquid could spill via the second opening 614. Conversely, the amount of possible spillage of the at least first amount of liquid 601 via the second opening 614 is reduced when the gas removal apparatus 600 is in the liquid receiving position 616 (e.g., FIG. 4C). It is typically desired that minimal leakage of liquid occur from the gas removal apparatus 600 so as to not needlessly dampen the surrounding sterile environment. If the second opening 614 is capable of behaving like a fluid drain, a positioning similar to the liquid receiving position 616 may be preferable when removing the at least the first part of the medical device (e.g., manipulable portion 300 or structure 308) from the gas removal apparatus 600 according to some embodiments. It is noted that in some embodiments, the gas removal apparatus 600 may be operable to laterally drain liquid in the interior chamber 603 through the second opening 614 when the gas removal apparatus 600 is in (c) the liquid receiving position 616, or (d) the another position 618 different from the liquid receiving position 616, or in each of (c) and (d). For example, in each of FIGS. 4C and 4D, second opening 614 is oriented (if second opening 614 were to function as a liquid drain) to laterally drain (e.g., with respect to the vertically upward direction exemplified by arrow 606) liquid in each of the liquid receiving position 616 and the another position 618 different from the liquid receiving position 616.

According to some embodiments, the gas removal apparatus 600 may be configured such that the second opening 614 is disposed below the uppermost surface 601b of the at least the first amount of liquid 601 present in the interior chamber 603 when the gas removal apparatus 600 is arranged in the another position 618 different from the liquid receiving position 616 in the state where (i) the at least the first amount of liquid 601 is present in the interior chamber 603 and (ii) the at least part of the medical device (e.g., manipulable portion 300 or structure 308) protrudes into the interior chamber 603 via the second opening 614 and is positioned at the particular location 617 and in a particular configuration in the interior chamber 603 (for example, as shown in FIG. 4D). In some embodiments, the gas removal apparatus 600 is configured such that at least part of second opening 614 is disposed above the uppermost surface 601a of the at least the first amount of the liquid 601 present in the interior chamber 603 when the gas removal apparatus 600 is arranged in the liquid receiving position 616 in the state where (a) the at least the first amount of liquid 601 is present in the interior chamber 603, and (b) the at least part of the medical device (e.g., manipulable portion 300 or structure 308) protrudes into the interior chamber 603 via the second opening 614 and is positioned at a particular location 617 and in a particular configuration in the interior chamber 603 (for example, as shown in FIG. 4C). In some embodiments, the entirety of the second opening 614 is disposed above the uppermost surface 601a of the at least the first amount of the liquid 601 present in the interior chamber 603 when the gas removal apparatus 600 is arranged in the liquid receiving position 616 in the state where (a) the at least the first amount of liquid 601 is present in the interior chamber 603, and (b) the at least part of the medical device (e.g., manipulable portion 300 or structure 308) protrudes into the interior chamber 603 via the second opening 614 and is positioned at a particular location 617 and in a particular configuration in the interior chamber 603.

In some embodiments, the gas removal apparatus 600 may be configured such that the first opening 607 is disposed above the uppermost surface 601b of the at least the first amount of liquid 601 present in the interior chamber 603 when the gas removal apparatus 600 is arranged in the another position 618 different from the liquid receiving position 616 in the state where (i) the at least the first amount of liquid 601 is present in the interior chamber 603 and (ii) the at least part of the medical device (e.g., manipulable portion 300 or structure 308) protrudes into the interior chamber 603 via the second opening 614 and is positioned at the particular location 617 and in a particular configuration in the interior chamber 603 (for example, as shown in FIG. 4D). In some embodiments, the gas removal apparatus 600 is configured such that the first opening 607 is disposed above the second opening 614 when the gas removal apparatus 600 is arranged in the another position 618 different from the liquid receiving position 616 in the state where (i) the at least the first amount of liquid 601 is present in the interior chamber 603 and (ii) the at least part of the medical device (e.g., manipulable portion 300 or structure 308) protrudes into the interior chamber 603 via the second opening 614 and is positioned at the particular location 617 and in a particular configuration in the interior chamber 603 (for example, as shown in FIG. 4D).

According to some embodiments, the gas removal apparatus 600 may be configured such that the second opening 614 is located at least proximate the uppermost surface 601a of the at least the first amount of liquid 601 present in the interior chamber 603 when the gas removal apparatus 600 is arranged in the liquid receiving position 616 in the state where (a) the at least the first amount of liquid 601 is present in the interior chamber 603, and (b) the at least part of the medical device (e.g., manipulable portion 300 or structure 308) protrudes into the interior chamber 603 via the second opening 614 and is positioned at a particular location 617 and in a particular configuration in the interior chamber 603 (for example, as shown in FIG. 4C).

According to various embodiments, the at least part of the medical device (e.g., manipulable portion 300 or structure 308) may be selectively movable between a first configuration where the at least the first part of the medical device (e.g., manipulable portion 300 or structure 308) is sized to be deliverable through the second opening 614 into the interior chamber 603, and a second configuration where the at least the first part of the medical device (e.g., manipulable portion 300 or structure 308) is sized too large to be deliverable through the second opening 614 into the interior chamber 603. In some embodiments, the at least the part of the medical device (e.g., manipulable portion 300 or structure 308) is in the second configuration in the interior chamber 603 (for example, as shown in FIGS. 4C and 4D). It is noted that in some embodiments, the first configuration may correspond to a delivery configuration (for example, as described above). It is noted that in some embodiments, the second configuration may correspond to an expanded or deployed configuration (for example, as described above). In some embodiments, the first configuration and the delivery configuration may be different configurations. For example, the at least the part of the medical device (e.g., manipulable portion 300 or structure 308) may be suitably sized to pass through the second opening 614 in the first configuration, but may be sized too large to pass through a particular bodily opening (or catheter sheath) for which the delivery configuration is appropriately sized for. In other words, the second opening 614 and the bodily opening or a catheter sheath opening may be different in size, and thus may place different sizing requirements of the at least the part of the medical device for delivery therethrough. In some embodiments, the second configuration and the expanded or deployed configuration may be different configurations. For example, the expanded or deployed configuration may be a specific configuration in which the at least the part of the medical device (e.g., manipulable portion 300 or structure 308) is in an intended operational configuration (e.g., an intended operational configuration in which the at least the part of the medical device is operated to transmit energy (e.g., ablative energy) or an intended operation configuration in which the at least the part of the medical device is configured for implantation), while the second configuration is not an intended operational configuration. It is noted that in various embodiments, the use of the second configuration when the at least the part of the medical device is in the interior chamber may be motivated for different reasons. For example, the second configuration may reduce the number or size of particular regions of the at least the part of the medical device that may trap gas bubbles during a gas bubble removal procedure such as described below.

According to some embodiments, the particular configuration in the interior chamber 603 includes a particular orientation of the at least the part of the medical device (e.g., manipulable portion 300 or structure 308) with respect to the interior chamber 603 that is the same in each of the liquid receiving position 616 and the another position 618 different from the liquid receiving position 616. This may occur, for example, when no relative movement between the at least the part of the medical device (e.g., manipulable portion 300 or structure 308) and the interior chamber 603 accompanies a movement of the gas removal apparatus 600 from the liquid receiving position 616 to the another position 618 different from the liquid receiving position 616. For example, a comparison of FIGS. 4C and 4D shows the manipulable portion 300 having a substantially similar orientation with respect to, or relative to, the interior chamber 603 in each of the liquid receiving position 616 and the another position 618 different from the liquid receiving location 616.

In other embodiments, the particular configuration in the interior chamber 603 includes a particular orientation of the at least the part of the medical device (e.g., manipulable portion 300 or structure 308) with respect to the interior chamber 603 that is different in each of the liquid receiving position 616 and the another position 618 different from the liquid receiving position 616. This may occur, for example, when relative movement between the at least part of the medical device (e.g., manipulable portion 300 or structure 308) and the gas removal apparatus 600 occurs during or after a movement of the gas removal apparatus 600 between the liquid receiving position 616 and the another position 618 different from the liquid receiving position 616. By way of non-limiting example, relative movement between the at least part of the medical device (e.g., manipulable portion 300 or structure 308) and the gas removal apparatus 600 may be achieved by holding the medical device substantially stationary during a rotation (e.g., represented by arrow 620) of the gas removal apparatus 600 between the liquid receiving position 616 and the another position 618 different from the liquid receiving position 616. In this regard, the gas removal apparatus 600 may rotate about the medical device at location defined by the second opening 614.

According to some embodiments, the gas removal apparatus 600 may include one or more first contact surfaces 622 (FIGS. 4B, 4C and 4D) configured to contact a supporting object 625 (FIGS. 4C, 4D) when the gas removal apparatus 600 is arranged in the liquid receiving position 616 while supported by the supporting object 625. According to some embodiments, the gas removal apparatus 600 may include one or more second contact surfaces 624 (FIGS. 4B, 4C and 4D) configured to contact a supporting object 625 (FIGS. 4C, 4D) when the gas removal apparatus 600 is arranged in the another position 618 different from the liquid receiving position 616 while supported by the supporting object 625. In some embodiments, the one or more first contact surfaces 622 is/are arranged to contact the supporting object 625 at each of a first set of three or more points of contact when the gas removal apparatus 600 is arranged in the liquid receiving position 616 while supported by the supporting object 625, and at least three points of contact of the first set of three or more points of contact are arranged non-colinearly. In some embodiments, the one or more second contact surfaces 624 is/are arranged to contact the supporting object 625 at each of a first set of three or more points of contact when the gas removal apparatus 600 is arranged in the another position 618 different from the liquid receiving position 616 while supported by the supporting object 625, and at least three points of contact of the second set of three or more points of contact are arranged non-colinearly. Having at least three points of contact arranged non-colinearly better supports the gas removal apparatus 600 while supported on the supporting object 625 in either of the liquid receiving position 616 or the another position 618 different from the liquid receiving position 616.

In some embodiments, each of at least one surface of the one or more first contact surfaces 622 may oppose the filling surface 605 across the interior chamber 603 (for example, as exemplified in FIGS. 4C and 4D). In some embodiments, the filling surface 605 and at least one first contact surface among the one or more first contact surfaces 622 oppose each other for a first distance. For example, in FIG. 4C, the filling surface 605 and at least one first contact surface of the one or more first contact surfaces 622 oppose each other for at least a first distance indicated as $D_1$. In some embodiments, a second distance between the filling surface 605 and the at least one first contact surface increases as at least part of the first distance $D_1$ is traversed away from the end of the filling surface 605 where the first opening 607 is arranged. For example, in FIG. 4C, a second distance indicated as $D_2$ between the filling surface 605 and the at least first contact surface of the one or more first contact surfaces 622 increases as at least part of the first distance $D_1$ is traversed away from the end of the filling surface 605 where the first opening 607 is arranged.

In some embodiments, the filling surface 605 has a sloped orientation relative to (c) at least one of the one or more first contact surfaces 622, (d) at least one of the one or more second contact surfaces 624, or both (c) and (d) (for example, as exemplified in FIGS. 4C and 4D). In some embodiments, each of (c) the filling surface 605 and (d) at least one surface of the one or more first contact surfaces 622 has a sloped orientation relative to each of at least one surface of the one or more second contact surfaces 624. The use of the various sloped orientations described above may be motivated for various reasons. For example, the filling surface 605 has a sloped orientation relative to the one or more first contact surfaces 622 to facilitate a flow of received liquid along the filling surface 605 toward first opening 607 when the gas removal apparatus 600 is in the liquid receiving position 616 according to some embodiments. However, according to some embodiments, it is desired that respective wall portions of the gas removal chamber 600 associated with filling surface 605 and the one or more first contact surfaces 622 be vertically oriented or that they slope outwardly away from each other in the another position 618 different from the liquid receiving position 616. This particular "vertical" or "sloping apart (e.g., divergent sloped)" orientation of the respective wall portions in the another position 618 different from the liquid receiving position 616 may be motivated for various reasons including reducing the occurrences of gas bubbles clinging to the wall portions during the gas removal procedure. It is noted that that gas bubbles will have a higher affinity to cling to a wall portion, the more the wall slopes inwardly into the interior chamber 603 to act as a trap that interrupts movement of gas bubbles that are released and travel upward due to buoyancy forces during the gas removal procedure. In some embodiments, a desire to have the particular wall portion providing the filling surface 605 slope toward the interior chamber 603 in the liquid receiving position 616 conflicts with a desire to have the particular wall portion be oriented vertically or sloping away from the interior chamber 603 in the another position 618 different from the liquid receiving position 616 to reduce gas bubble accumulation. According to some embodiments, a particular orientation between the filling surface 605 and the one or more second contact surfaces 624 is configured to reduce an angular deviation from plumb of the filling surface 605 when the gas removal apparatus 600 is in the another position 618 while maintaining a desired sloped orientation from level when the gas removal apparatus 600 is in the liquid receiving position 616. This can be achieved in various manners according to some embodiments. For example, in some embodiments, the filling surface 605 is configured to be out of level by a first angular amount (e.g., $\theta_1$ in FIG. 4C) when the gas removal apparatus 600 is arranged in the liquid receiving position 616 on a level surface, and each of at least one of the one or more second contact surfaces 624 is configured to be out of plumb by a second angular amount (e.g., $\theta_2$ in FIG. 4C) when the gas removal apparatus 600 is arranged in the liquid receiving position 616 on a level surface. According to various embodiments, the first angular amount (e.g., $\theta_1$ in FIG. 4C) is different from the second angular amount (e.g., $\theta_2$ in FIG. 4C). According to some embodiments, a magnitude of the first angular amount (e.g., $\theta_1$ in FIG. 4C) is greater than a magnitude of the second angular amount (e.g., $\theta_2$ in FIG. 4C). According to some embodiments, a magnitude of the first angular amount (e.g., $\theta_1$ in FIG. 4C) is nominally twice the magnitude of the second angular amount (e.g., $\theta_2$ in FIG. 4C). It is noted that in embodiments in which a magnitude of the first angular amount (e.g., $\theta_1$ in FIG. 4C) is nominally twice the magnitude of the second angular amount (e.g., $\theta_2$ in FIG. 4C), an angular deviation of the filling surface 605 from plumb (e.g., $\theta_3$ in FIG. 4D) is reduced to half of $\theta_1$ (i.e., the slope angle of the filling surface 605 in the liquid receiving position 616) when the gas removal apparatus 600 is arranged on a level surface in the another position 618 different from the liquid receiving position 616, thereby advantageously reducing gas bubbles clinging effects during a gas removal procedure.

The various orientations between the filling surface 605 and the one or more second contact surfaces 624 described above, may cause, according to some embodiments, respective wall portions including the one or more first contact surfaces 622 to deviate from plumb when the gas removal apparatus 600 is arranged on a level surface in the another position 618 different from the liquid receiving position 616.

In some embodiments, (c) the filling surface 605 is configured to slope toward the one or more first contact surfaces 622 as the filling surface 605 extends upward when the gas removal apparatus 600 is arranged in the another position 618 different from the liquid receiving position 616, (d) the one or more first contact surfaces 622 are configured to slope toward the filling surface 605 as the one or more first contact surfaces 622 extend upward when the gas removal apparatus 600 is arranged in the another position 618 different from the liquid receiving position 616, or both (c) and (d) (for example as exemplified in FIG. 4D). In some embodiments, the filling surface 605 is configured to be out of plumb by a first angular amount (e.g., $\theta_3$ in FIG. 4D) when the gas removal apparatus 600 is arranged in the another position 618 different from the liquid receiving position 616 on a level surface, and wherein each of at least one of the one or more first contact surfaces 622 is out of plumb by a second angular amount (e.g., $\theta_4$ in FIG. 4D) when the gas removal apparatus 600 is arranged in the another position 618 different from the liquid receiving position 616 on the level surface. In some embodiments, the first angular amount may be substantially equal to the second angular amount. For example, in FIG. 4D, the first angular amount (e.g., $\theta_3$) may be substantially equal to the second angular amount (e.g., $\theta_4$). In some embodiments, the first angular amount varies by no more than twenty percent of the second angular amount, or the second angular amount varies by no more than twenty percent of the first angular amount.

According to some embodiments, a surface of the gas removal apparatus 600 other than the filling surface 605 includes the second opening 614. For example, in FIGS. 4A and 4B, surface 626 of the gas removal apparatus 600 includes, or is intercepted by, second opening 614, surface 626 being other than filling surface 605. According to various embodiments, surface 626 is not configured to receive the at least the first amount of liquid 601 and flow therealong to the interior chamber 603 (e.g., via first opening 607) when the gas removal apparatus 600 is arranged in the liquid receiving position 616. According to various embodiments, a surface (e.g., 626) of the gas removal apparatus 600 other than the filling surface 605, any surface of the one or more first contact surfaces 622, or any surface of the one or more second contact surfaces 624 includes the second opening 614. In some embodiments, a shape of the first opening 607 is different from a shape of the second opening 614. For example, as seen in FIGS. 4A and 4B, first opening 607 includes an elongated shape whereas second opening 614 includes a circular shape, according to some embodiments.

According to some embodiments, a gas removal apparatus 600 configured to receive a first amount of liquid 601 effective to remove gas bubbles from at least a part of a medical device (e.g., manipulable portion 300 or structure 308) removably disposed in the gas removal apparatus 600 may include a wall portion that includes a first surface and a second surface opposite across a thickness of the wall portion from the first surface. For example, in FIGS. 4E and 4F, gas removal apparatus 600 includes an exemplary wall portion 630 including a first surface 630a and a second surface 630b opposite across a thickness 630c of the wall portion 630 according to some embodiments. In some embodiments, the first surface 630a of wall portion 630 may be configured to receive the at least the first amount of liquid 601 and cause the received at least the first amount of liquid 601 to flow along the first surface 630a of the wall portion 630 to the interior chamber 603 of the gas removal apparatus 600 when the gas removal apparatus 600 is arranged in a liquid receiving position (e.g., 616, described above). According to some embodiments, the first surface 630a of the wall portion 630 may be provided by the filling surface 605 described above. According to some embodiments, the second surface 630b of the wall portion 630 is configured to define at least part of the interior chamber 603 of the gas removal apparatus 600.

According to some embodiments, at least a portion of the second surface 630b of the wall portion 630 is configured, when the gas removal apparatus 600 is arranged in the liquid receiving position 616 in a state where the at least the first amount of liquid 601 is present in the interior chamber 603, to not contact the at least the first amount of liquid 601 present in the interior chamber 603. For example, in FIG. 4E, an entirety of the second surface 630b does not contact the at least the first amount of liquid 601 present in the interior chamber 603 when the gas removal apparatus 600 is in the liquid receiving position 616. According to some embodiments, no portion of the wall portion 630 is configured to, when the gas removal apparatus 600 is arranged in the liquid receiving position 616 in a state where the at least the first amount of liquid 601 is present in the interior chamber 603, contact the at least the first amount of liquid 601 present in the interior chamber 603. It is noted however, that in some embodiments, the at least the portion of the second surface 630b of the wall portion that is configured to not contact the first amount of liquid 601 present in the interior chamber 603 when the gas removal apparatus 600 is in the liquid receiving position 616 may include some but not all of the second surface 630b of the wall portion 630. For example, if the first amount of liquid 601 present in the interior chamber 603 in FIG. 4E is increased up to first opening 607 (first opening 607 described in further detail below), contact between part of the second surface 630b proximate the first opening 607 and the at least the first amount of liquid 601 may be present, but an entrapped air pocket may prevent contact between the liquid 601 and the remaining portion of the second surface 630b when the gas removal apparatus is in the liquid receiving position 616. In FIG. 4E, the at least the portion of the second surface 630b of the wall portion 630 configured to, when the gas removal apparatus 600 is arranged in the liquid receiving position 616 in the state where the at least the first amount of liquid 601 is present in the interior chamber 603, not contact the at least the first amount of liquid 601 present in the interior chamber 603 is indicated as 630b-1 according to some embodiments. According to some embodiments, the at least the portion 630b-1 of the second surface 630b of the wall portion 630 is configured to, when the gas removal apparatus 600 is arranged in another position different from the liquid receiving position (e.g., 616) in the state where the at least the first amount of liquid 601 is present in the interior chamber 603, contact the at least the first amount of liquid 601 present in the interior chamber 603. For example, in FIG. 4F, the at least the portion 630b-1 of the second surface 630b of the wall portion 630 is configured to, when the gas removal apparatus 600 is arranged in another position 618 (described above) different from the liquid receiving position 616 in the state where the at least the first amount of liquid 601 is present in the interior chamber 603, contact the at least the first amount of liquid 601 present in the interior chamber 603. It is noted that in some embodiments, gas removal or flushing from the at least the part of the medical device (e.g., manipulable portion 300 or structure 308) may occur when the gas removal apparatus 600 is arranged in the another position 618 different from the liquid receiving position 616 (for example, as described in greater detail below).

According to some embodiments, the gas removal apparatus 600 may include a first opening (e.g. 607) arranged at end of the wall portion 630 and configured to provide a first path (exemplified in FIG. 4E by 608) into the interior chamber 603. According to some embodiments, the first surface 630a of the wall portion 630 is configured such that the received at least the first amount of liquid 601 caused to flow along the first surface 630a of the wall portion 630 to the interior chamber 603 when the gas removal apparatus 600 is arranged in the liquid receiving position 616 enters the interior chamber 603 via the first path provided by the first opening 607. According to some embodiments, the gas removal apparatus 600 may include a second opening (e.g., 614) configured to provide a second path (exemplified in FIGS. 4A and 4B by 615) into the interior chamber 603 and configured to receive the medical device such that the at least part of the medical device (e.g., manipulable portion 300 or structure 308) enters the interior chamber 603 via the second path provided by the second opening 614. According to some embodiments, the first path into the interior chamber 603 and the second path into the interior chamber 603 are mutually exclusive paths into the interior chamber 603. In some embodiments, a shape of the first opening 607 is different from a shape of the second opening 614. For example, as seen in FIGS. 4A and 4B, first opening 607 includes an elongated shape whereas second opening 614 includes a circular shape, according to some embodiments.

According to some embodiments, first opening 607 is arranged at an end of the wall portion 630 and is configured to provide a first path into the interior chamber 603, and the first surface 630a of the wall portion 630 is configured such that the received at least the first amount of liquid 601 caused to flow along the first surface 630a of the wall portion 630 to the interior chamber 603 when the gas removal apparatus 600 is arranged in the liquid receiving position 616 enters the interior chamber 603 via the first path provided by the first opening 607. In some embodiments, the first opening 607 is an elongated opening arranged between the end of the first surface 630a of the wall portion 630 and one or more third surfaces 610 of the gas removal apparatus 600 such that the liquid flowing along the first surface 630a of the wall portion 630 enters the interior chamber 603 via the elongated opening. According to some embodiments, at least some of the received at least the first amount of liquid 601 caused to flow along the first surface 630a and enter the interior chamber 603 via the elongated opening is then caused to flow along at least a portion of at least one third surface of the one or more third surfaces 610 of the gas removal apparatus 600.

According to some embodiments, the first surface 630a of the wall portion 630 may be an external surface of the gas removal apparatus 600. This may be motivated for different reasons. For example, as an external surface, the first surface 630a may be better suited to receiving the at least the first amount of liquid 601 by a pouring action (for example, in a manner similar or identical as described above with respect to filling surface 605). According to some embodiments, the gas removal apparatus 600 is configured such that, when arranged in the liquid receiving position 616 in the state where the at least the first amount of liquid 601 is present in the interior chamber 603, the first surface 630a of the wall portion 630, the second surface 630b, or each of both the first surface 630a of the wall portion 630 and the second surface 630b of the wall portion 630 has a sloped orientation relative to an uppermost surface (e.g., 601a in FIG. 4E) of the at least the first amount of liquid 601 present in the interior chamber 603. The sloped orientation may be motivated for various reasons. For example, the sloped orientation may assist in allowing the at least the first amount of liquid 601 received by the first surface 630a of the wall portion 630 to flow along the first surface 630a to the interior chamber 603. In some embodiments, the second surface 630b of the wall portion 630 and an interior surface (e.g., interior surface 631 in FIG. 4E) opposite across the interior chamber 603 from the second surface 630b of the wall portion 630 oppose each other for a first distance (e.g., distance $D_3$ indicated in FIG. 4E), and a second distance (e.g., distance $D_4$ indicated in FIG. 4E) between the second surface 630b of the wall portion 630 and the interior surface increases as at least part of the first distance is traversed away from an opening (e.g., first opening 607) arranged at an end of the wall portion 630, the opening configured to provide a first path into the interior chamber 603.

In some embodiments, the gas removal apparatus 600 may include one or more first contact surfaces 622 configured to contact a supporting object (e.g., 625 in FIGS. 4E and 4F) when the gas removal apparatus 600 is arranged in the another position 618 different from the liquid receiving position 616 while supported by the supporting object (e.g., 625). In some embodiments, the gas removal apparatus 600 may include one or more second contact surfaces 624 configured to contact the supporting object (e.g., 625) when the gas removal apparatus 600 is arranged in the another position (e.g., 618) different from the liquid receiving position 616 while supported by the supporting object (e.g., 625). In some embodiments, each of at least one surface of the one or more first contact surfaces 622 opposes the second surface 630b across the interior chamber 603.

Figure 4F:
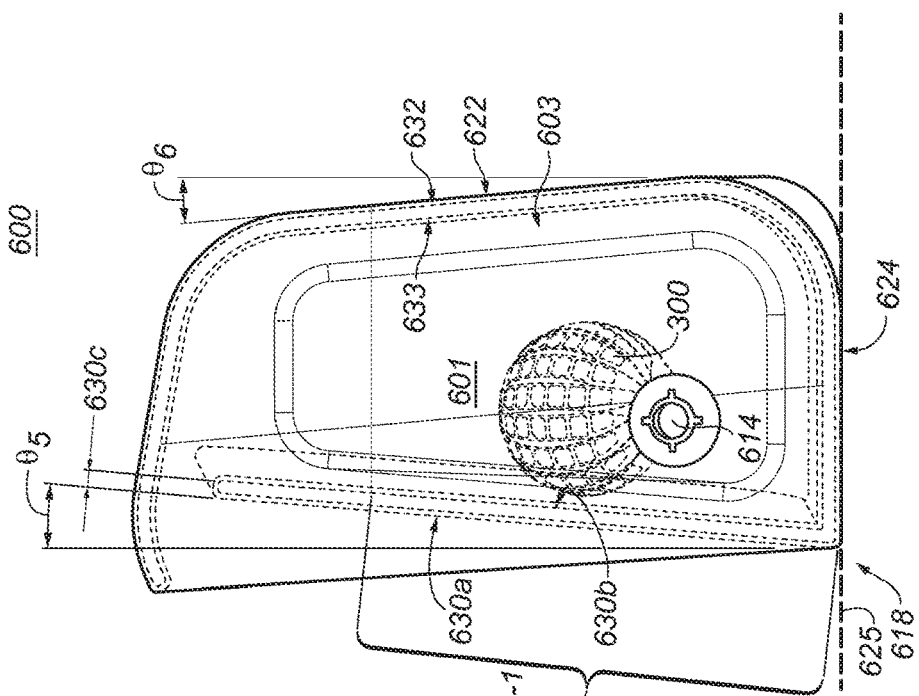
FIG. 4F is a side view of a gas removal apparatus positioned in another position different from a liquid receiving position according to some embodiments.
Figure 4E:
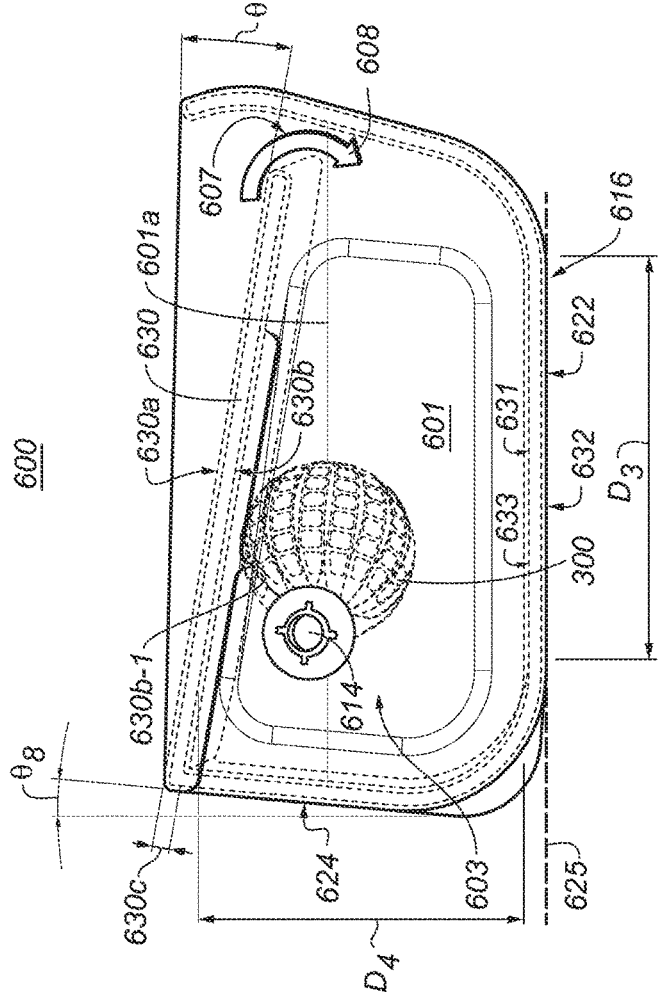
FIG. 4E is a side view of a gas removal apparatus positioned in a liquid receiving position according to some embodiments.

In some embodiments, the first surface 630a of the wall portion 630, the second surface 630b of the wall portion 630, or each of both the first surface 630a of the wall portion 630 and the second surface 630b of the wall portion 630 has a sloped orientation relative to a) each of at least one of the one or more first contact surfaces 622, b) each of at least one of the one or more second contact surfaces 624, or both a) and b) (for example, as shown in FIGS. 4E and 4F). According to some embodiments, a) the first surface 630a of the wall portion 630, the second surface 630b of the wall portion 630, or each of both the first surface 630a of the wall portion 630 and the second surface 630b of the wall portion 630 slope toward each of at least one surface of the one or more first contact surfaces 622 as the wall portion 630 extends upward when the gas removal apparatus 600 is arranged in the another position 618 (e.g., FIG. 4F) different from the liquid receiving position 616 while supported by the supporting object (e.g., 625), b) each of at least one surface of the one or more first contact surfaces 622 slope toward the first surface 630a of the wall portion 630, the second surface 630b of the wall portion 630, or each of both the first surface 630a of the wall portion 630 and the second surface 630b of the wall portion 630 as the one or more first contact surfaces 622 extend upward when the gas removal apparatus 600 is arranged in the another position 618 different from the liquid receiving position 616 while supported on the supporting object (e.g., 625), or both a) and b).

In some embodiments, another wall portion (e.g., 632 in FIGS. 4E and 4F) includes the one or more first contact surfaces 622 and a third surface 633 opposite across a thickness of the another wall portion 632 from the one or more contact surfaces 622. In some embodiments, the third surface 633 defines at least part of the interior chamber 603. In some embodiments, the first surface 630a of the wall portion 630, the second surface 630b of the wall portion 630, or each of both the first surface 630a of the wall portion 630 and the second surface 630b of the wall portion 630 is configured to be out of plumb by a first angular amount when the gas removal apparatus 600 is arranged in the another position 618 different from the liquid receiving position 616 on a level surface. For example, in FIG. 4F, second surface 630b is configured to be out of plumb by first angular amount $\theta_5$ when the gas removal apparatus 600 is arranged in the another position 618 different from the liquid receiving position 616 on a level surface. In some embodiments, the third surface 633 of the another wall portion 632 is configured to be out of plumb by a second angular amount when the gas removal apparatus 600 is arranged in the another position 618 different from the liquid receiving location 616 on a level surface. For example, in FIG. 4F, the third surface 633 is configured to be out of plumb by second angular amount $\theta_6$ when the gas removal apparatus 600 is arranged in the another position 618 different from the liquid receiving position 616 on a level surface. In some embodiments, the first angular amount $\theta_5$ is substantially equal to the second angular amount $\theta_6$. In some embodiments, the first angular amount $\theta_5$ varies by no more than twenty percent of the second angular amount $\theta_6$, or the second angular amount $\theta_6$ varies by no more than twenty percent of the first angular amount $\theta_5$.

According to some embodiments, the first surface 630a of the wall portion 630, the second surface 630b of the wall portion 630, or each of both the first surface 630a of the wall portion 630 and the second surface 630b of the wall portion 630 is configured to be out of level by a first angular amount when the gas removal apparatus 600 is in the liquid receiving position 616 on a level surface. For example, in FIG. 4E, the first surface 630a of the wall portion 630 is configured to be out of level by a first angular amount $\theta_7$ when the gas removal apparatus 600 is in the liquid receiving position 616 on a level surface. According to some embodiments, at least one surface of the one or more second contact surfaces 624 is configured to be out of plumb by a second angular amount when the gas removal apparatus 600 is the liquid receiving position 616 on a level surface. For example, in FIG. 4E, at least one surface of the one or more second contact surfaces 624 is configured to be out of plumb by a second angular amount $\theta_8$ when the gas removal apparatus 600 is in the liquid receiving position 616 on a level surface. According to some embodiments, the first angular amount $\theta_7$ is different from the second angular amount $\theta_8$. According to some embodiments, a magnitude of the first angular amount $\theta_7$ is greater than a magnitude of the second angular amount $\theta_8$. According to some embodiments, a magnitude of the first angular amount $\theta_7$ is nominally twice the magnitude of the second angular amount $\theta_8$. These various relationships between the first angular amount $\theta_7$ and the second angular amount $\theta_8$ may be motivated for various reasons including reasons similar to, or identical to, various embodiments described above with respect to FIGS. 4C and 4D.

In some embodiments, the one or more first contact surfaces 622 is/are arranged to contact the supporting object (e.g., 625) at each of a first set of three or more points of contact when the gas removal apparatus 600 is arranged in the liquid receiving position 616 while supported by the supporting object. In some embodiments, at least three points of contact of the first set of three or more points of contact are arranged non-colinearly. According to some embodiments, the one or more second contact surfaces 624 is/are arranged to contact the supporting object (e.g., 625) at each of a second set of three or more points of contact when the gas removal apparatus 600 is arranged in the another position 618 different from the liquid receiving position 616 while supported by the supporting object. In some embodiments, at least three points of contact of the second set of three or more points of contact are arranged non-colinearly.

Figure 4G:
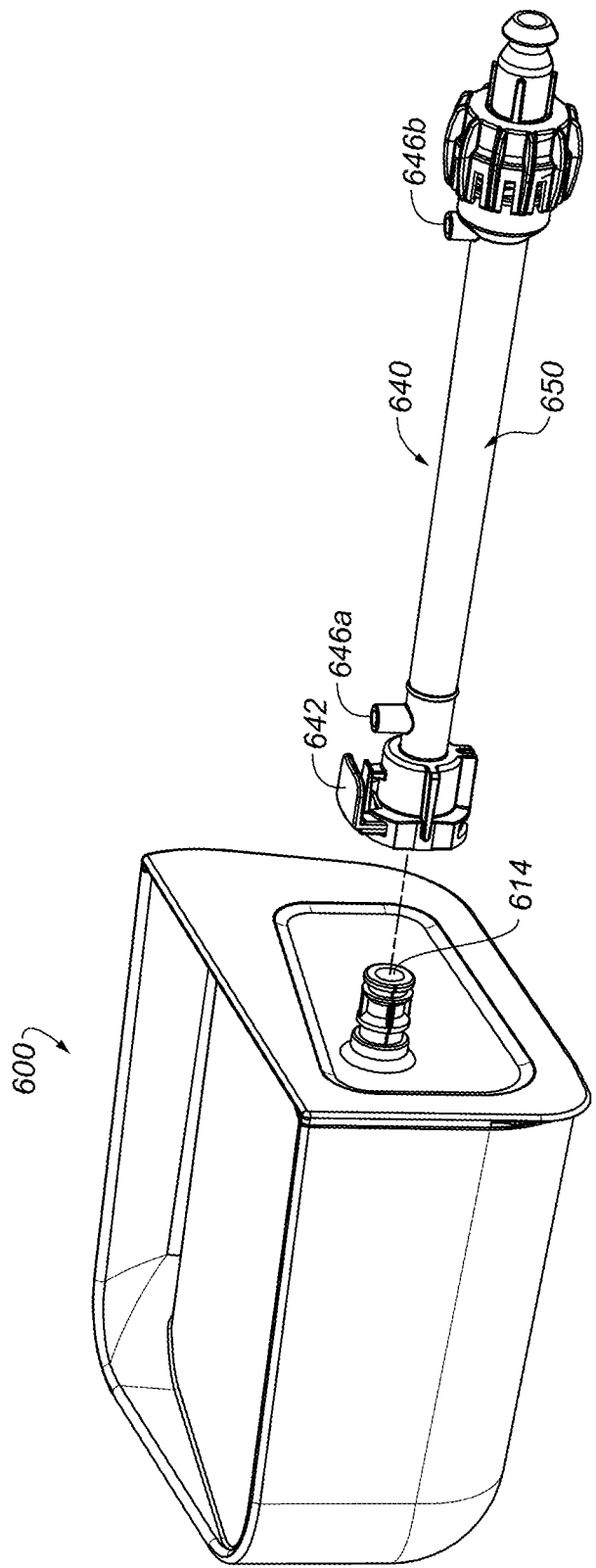
FIG. 4G is a view of the gas removal apparatus of FIG. 4A including a loading assembly according to some embodiments.

Turning to FIG. 4G, a loading assembly 640 may be provided to assist insertion of a least part (e.g., manipulable portion 300 or structure 308) of the medical device into the gas removal apparatus 600 (for example, into the interior chamber 603 of the gas removal apparatus 600). In some embodiments, loading assembly 640 may be provided to assist insertion of a least part (e.g., manipulable portion 300 or structure 308) of the medical device into a catheter sheath (e.g., 312). In this regard, according to some embodiments, loading assembly 640 may be removably attached to gas removal apparatus 600 at least via coupler 642 located on a distal portion of the loading assembly 640. At least one seal 644 (e.g., an elastomeric seal) (FIGS. 4H-4J) may be employed to reduce or eliminate potential fluid leaks between gas removal apparatus 600 and loading assembly 640. As described below with reference to FIGS. 4H, 4I, and 4J, the elongate shaft member (e.g., at least the elongate shaft member 314) may be inserted through a fluid vessel 650 of a loading assembly 640 to place at least part of the medical device (e.g., manipulable portion 300 or structure 308) into the interior chamber 603 of gas removing apparatus 600. A seal assembly 651 located, according to some embodiments, on a proximal portion of loading assembly 640 may be employed to reduce or eliminate potential fluid leaks at an interface between the loading assembly 640 and a portion of an elongate shaft member (e.g., 314) located in fluid vessel 650 of the loading assembly 640. According to some embodiments, loading assembly 640 may include a plurality of side ports 646a, 646b. The use of the side ports 646a, 646b may be motivated for various reasons. For example, according to some embodiments, after the at least part of the medical device (e.g., manipulable portion 300 or structure 308) has been flushed (e.g., as per method 700 described below) in the interior chamber 603 of the enclosure 602, the at least part of the medical device may be retracted (e.g., via translation of elongate shaft member (e.g., 314) to which the at least part of the medical device is physically coupled) into the loading assembly 640. The side ports 646a, 646b may be configured to be coupled to various liquid supplies or liquid drains to remove any air bubbles that may be present in the loader assembly 640, thereby allowing the flushed at least part of the medical device to be retracted into the loader assembly that has been filled with liquid and has been purged of air. The loading assembly 640 may then be physically coupled to the catheter sheath (e.g., 312) without unduly subjecting the at least part of the medical device to air.

Figure 5:
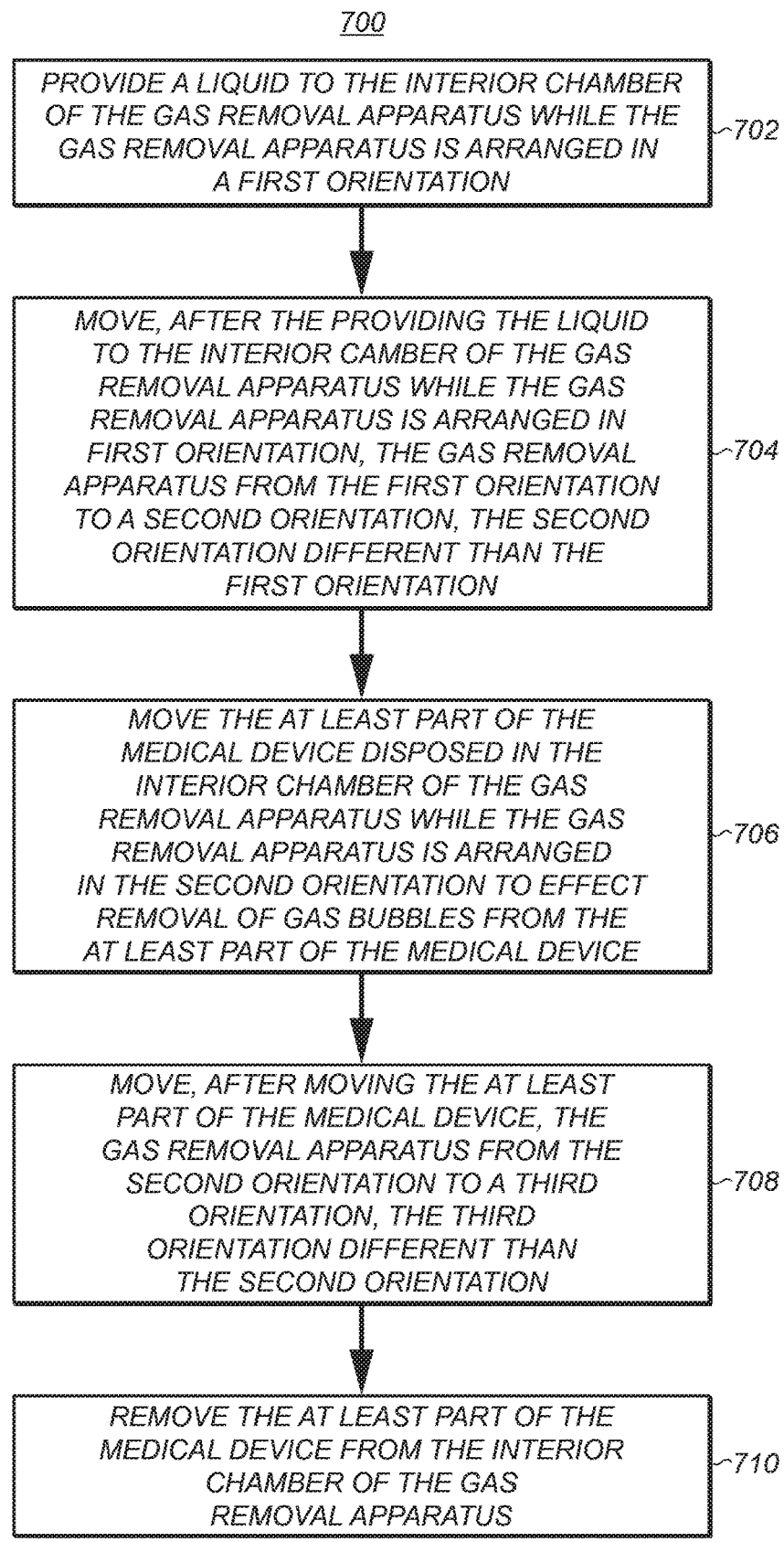
FIG. 5 illustrates a gas removal method, according to some embodiments.

FIG. 5 is a block diagram representing a gas removal (e.g., flushing) method 700 in which at least part of a medical device (e.g., manipulable portion 300) disposed in an interior chamber of a gas removal apparatus is flushed of an undesired fluid (e.g., air or other gases). For convenience of discussion, reference to gas removal apparatus 600 may be employed to describe actions described by various blocks associated with method 700. It is understood, however, that method 700 or variants thereof may be employed with other types of flushing apparatuses, according to various embodiments. It is also understood that not all actions that make up method 700 are necessary in all embodiments, the invention is not limited to the particular ordering of actions described with respect to method 700, and various embodiments may include different sequences of actions. It is noted that in some embodiments, the at least part of the medical device is received in the interior chamber (e.g., interior chamber 603)

at a place of use of the medical device. In some embodiments, the at least part of the medical device is received in the interior chamber (e.g., interior chamber 603) at a location remote from a particular location in which a medical procedure employing the medical device is conducted. For example, the at least part of the medical device may be received in the interior chamber (e.g., interior chamber 603) at a location where the medical device is manufactured or a location where gas removal apparatus (e.g., 600) is manufactured. According to various embodiments, the at least part of the medical device is received in the interior chamber (e.g., interior chamber 603) prior to the at least part of the medical device being inserted into the body of a patient. For instance, as discussed above, according to various embodiments, the manipulable portion 300 and structure 308 are not configured to operate on or interact with tissue of a bodily cavity in a state in which the manipulable portion 300 and structure 308 are located within the interior chamber 603 or any part of the gas removal apparatus 600. In other words, for example, the manipulable portion 300 and structure 308 are configured to operate on or interact with tissue of a bodily cavity in a state in which the manipulable portion 300 and structure 308 are not located within any part of the gas removal apparatus 600.

In some embodiments, the at least part of the medical device includes a distal end structure of a medical device (e.g., manipulable portion 300 or structure 308), the at least part of the medical device configured to be percutaneously delivered toward a bodily cavity distal end structure first. In some embodiments, the at least part of the medical device includes a structure (e.g., 218 or 308) including a plurality of transducers. In some embodiments, at least some of the transducers (e.g., 220 or 306) are operable to selectively emit tissue-ablative energy.

In some embodiments, the at least part of the medical device includes a structure (e.g., 218 or 308) that is selectively movable between a delivery configuration and a deployed configuration (examples of delivery and deployed configurations are discussed above). In some embodiments, the structure (e.g., 218 or 308) includes a plurality of elongate members (e.g., 304), a set of one or more transducers located on each of at least some of the plurality of elongate members. For example, as shown at least in FIG. 3, each elongate member 304 includes its own set of a plurality of transducers 306. In some embodiments, the structure includes an expandable balloon (e.g., a balloon catheter). In some embodiments, the at least part of the medical device includes an implant configured for implantation within the body of a patient.

Figure 4H:
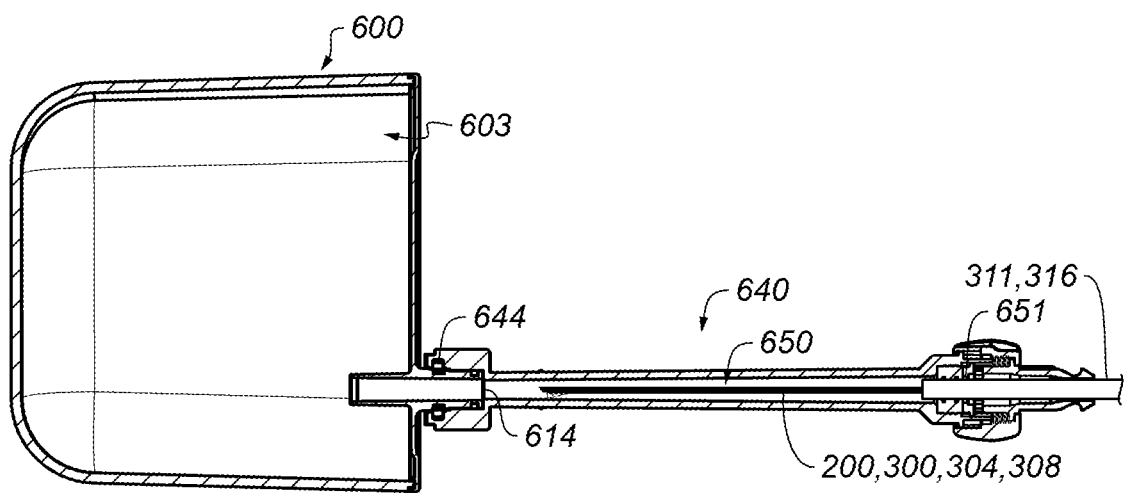
FIGS. 4H, 4I, and 4J are cutaway views of at least the gas removal apparatus of FIG. 4A, illustrating various states of insertion and expansion of a medical device within the gas removal apparatus, according to some embodiments.
Figure 4I:
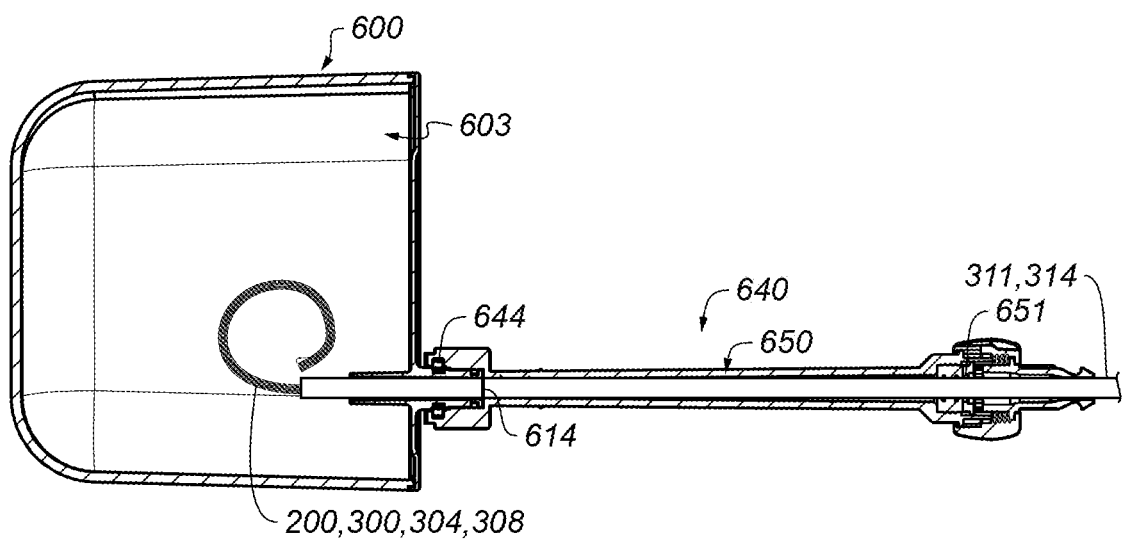
Figure 4J:
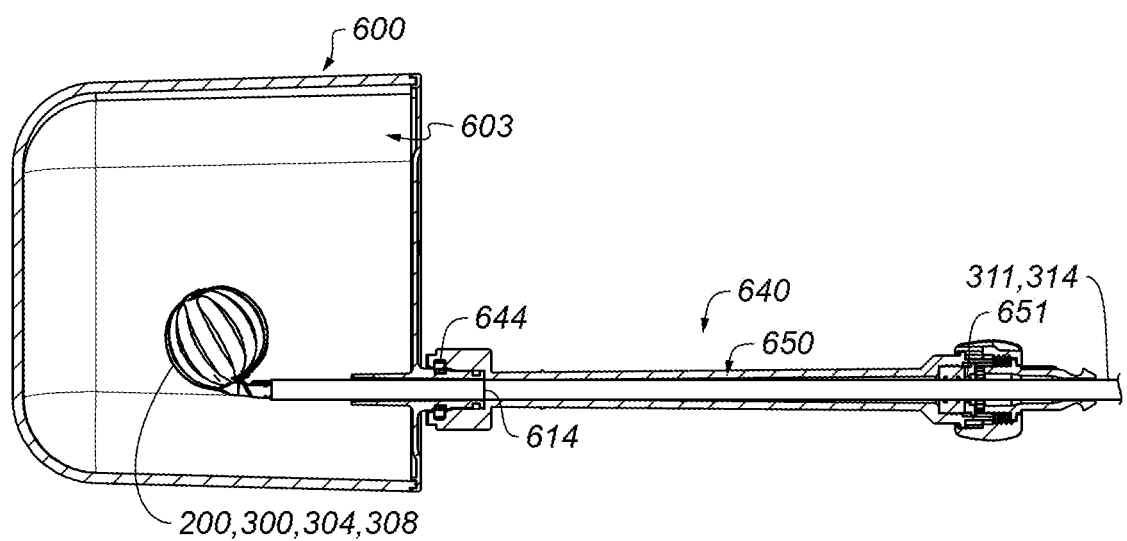

In some embodiments in which the at least part of the medical device (e.g., manipulable portion 300 or structure 308) is selectively movable between a delivery configuration and a deployed configuration (examples of delivery and deployed configurations are discussed above), the second opening 614 is sized to receive the at least part of the medical device in a state in which the at least part of the medical device is in the delivery configuration, but not the deployed configuration. For example, FIGS. 4H, 4I, and 4J show sectioned views of gas removal apparatus 600 at three separate times during an insertion of catheter 311 into gas removal apparatus 600, according to some embodiments. It is noted that loading assembly 640 (i.e., shown in section in FIGS. 4H, 4I, and 4J) also is employed for the insertion process, according to some embodiments. In FIG. 4H, the at least part of the medical device (e.g., manipulable portion 300 or structure 308) is shown in a delivery configuration in which the at least part of the medical device (e.g., manipulable portion 300 or structure 308) (i.e., shown positioned in loading assembly 640) is arranged in a suitable configuration (e.g., a stacked configuration) suitably sized to be deliverable through fluid vessel 650 of the loading assembly 640 and suitably sized to be deliverable through the second opening 614 of the gas removal apparatus 600. In FIG. 4I, the at least part of the medical device (e.g., manipulable portion 300 or structure 308) has been delivered into the interior chamber 603 and has been moved into a first deployed configuration (e.g., a coiled configuration) which causes the at least part of the medical device (e.g., manipulable portion 300 or structure 308) to have a size, according to some embodiments, too large to be deliverable through the loading assembly 640 and too large to be deliverable through the second opening 614 of the gas removal apparatus 600.

It is noted that the elongate members 304 that make up manipulable portion 300 or structure 308, according to various embodiments, are depicted schematically in FIGS. 4H and 4I, and manipulable portion 300 or structure 308 may include other elongate members 304 that are not shown.

In FIG. 4J, the at least part of the medical device (e.g., manipulable portion 300 or structure 308) has been delivered into the interior chamber 603 and has been moved into a second deployed configuration (e.g., a fanned configuration), which, like the first deployed configuration, is a configuration in which the at least the part of the medical device (e.g., manipulable portion 300 or structure 308) has a size, according to some embodiments, too large to be deliverable through the loading assembly 640 and too large to be deliverable through the second opening 614 of gas removal apparatus 600. In some embodiments, the at least part of the medical device (e.g., manipulable portion 300 or structure 308) is moved into the fanned second deployed configuration from the coiled first deployed configuration. In some embodiments, the at least part of the medical device (e.g., manipulable portion 300 or structure 308) is positioned in the deployed configuration in a state in which it is located within the flushing or interior chamber 603, as shown, e.g., in FIGS. 4I and 4J. U.S. Pat. No. 9,526,573, issued Dec. 27, 2016, which is hereby incorporated herein by reference in its entirety, describes various mechanisms and techniques by which a structure of a medical device may be manipulated and moved between various configurations.

In some embodiments, method 700 may include moving the at least part of the medical device (e.g., manipulable portion 300 or structure 308) between a delivery configuration and a deployed configuration within the interior chamber 603 of the gas removal apparatus 600. In some embodiments, method 700 may include moving the at least part of the medical device (e.g., manipulable portion 300 or structure 308) (a) from a delivery configuration to a deployed configuration within the interior chamber 603 of the gas removal apparatus 600, or (b) from a deployed configuration to a delivery configuration within the interior chamber 603 of the gas removal apparatus 600, or both (a) and (b). According to some embodiments, expanding movements of the at least part of the medical device within the interior chamber 603 of the gas removal apparatus 600 may facilitate flushing of undesired fluid (e.g., air) from the structure during the flushing procedures described herein.

Block 702 of method 700 includes providing a liquid to the interior chamber 603 of the gas removal apparatus 600 while the gas removal apparatus is arranged in a first orientation. According to various embodiments, the liquid may be a sterile liquid such a sterilized saline or sterilized heparinized saline. According to various embodiments, the provided liquid may enter the interior chamber 603 of the gas removal apparatus 600 via a first opening (e.g., first opening 607) provided in the gas removal apparatus 600 while the gas removal apparatus arranged in a first orientation. According to various embodiments, the first orientation may be associated with the liquid receiving position exemplified in FIGS. 4C and 4E. It is noted that the first orientation of the gas removal apparatus 600 includes any and all orientations or positions of the gas removal apparatus 600 that allow for providing a liquid to the interior chamber 603 of the gas removal apparatus 600 via a first opening (e.g., first opening 607) provided in the gas removal apparatus 600. Thus, the embodiments of FIGS. 4C and 4E each depict an example of an orientation or position of the gas removal apparatus 600 that allows for providing a liquid to the interior chamber 603 of the gas removal apparatus 600 via a first opening (e.g., first opening 607) provided in the gas removal apparatus 600.

According to various embodiments, the gas removal apparatus 600 may be supported on a supporting object while positioned in (with) the first orientation. In some embodiments, the gas removal apparatus 600 may be held by a user (e.g., a medical practitioner) while positioned in (with) the first orientation. According to some embodiments, the liquid may be provided to the interior chamber 603 of the gas removal apparatus 600 via a pouring action while the gas removal apparatus is arranged in a first orientation. According to some embodiments, the liquid may be provided to the interior chamber 603 of the gas removal apparatus 600 at a point of manufacture of the gas removal apparatus or a point of manufacture of the medical device. According to some embodiments, the liquid may be provided to the interior chamber 603 of the gas removal apparatus 600 at a location where a medical procedure employing the medical device is conducted (e.g., a point of use). According to some embodiments, the liquid may be provided to the interior chamber 603 of the gas removal apparatus 600 (e.g., while the gas removal apparatus is arranged in a first orientation) before the at least part of the medical device is inserted into the interior chamber 603 of the gas removal apparatus 600. According to some embodiments, the liquid may be provided to the interior chamber 603 of the gas removal apparatus 600 (e.g., while the gas removal apparatus is arranged in a first orientation) during, or after, an insertion of the at least part of the medical device into the interior chamber 603 of the gas removal apparatus 600. According to some embodiments, the at least part of the medical device (e.g., manipulable portion 300 or structure 308) may be disposed in an expanded or deployed configuration (e.g., FIG. 4I or 4J) in the interior chamber 603 of the gas removal apparatus 600, before, during, or after a providing of the liquid to the interior chamber 603 of the gas removal apparatus 600 while the gas removal apparatus is arranged in the first orientation. Block 704 of method 700 includes, according to various embodiments, moving, after the providing the liquid to the interior chamber. 603 of the gas removal apparatus 600 while the gas removal apparatus 600 is arranged in the first orientation, the gas removal apparatus 600 from the first orientation to a second orientation being different from the first orientation. For example, the gas removal apparatus 600 may be moved from a first orientation associated with a positioning of the gas removal apparatus 600 in the liquid receiving position 616 shown in FIG. 4C to a second orientation associated with a positioning of the gas removal apparatus 600 in the another position 618 different from the liquid receiving position 616 shown in FIG. 4D. According to some embodiments, the moving associated with block 704 may include a rotation (e.g., exemplified by arrow 620) of the gas removal apparatus 600.

It is noted that the second orientation of the gas removal apparatus 600 includes any and all orientations or positions of the gas removal apparatus 600 that allow for moving the at least the part of the medical device disposed in the interior chamber 603 of the gas removal apparatus 600 to effect removal of gas bubbles from the at least the part of the medical device due to an interaction between the at least the part of the medical device and the provided liquid present in the interior chamber 603 of the gas removal apparatus. Thus, the embodiments of FIGS. 4D and 4F each depict an example of an orientation or position of the gas removal apparatus 600 that allows for moving the at least the part of the medical device disposed in the interior chamber 603 of the gas removal apparatus 600 to effect removal of gas bubbles from the at least the part of the medical device due to an interaction between the at least the part of the medical device and the provided liquid present in the interior chamber 603 of the gas removal apparatus 600.

Block 706 of method 700 includes, according to various embodiments, moving the at least part of the medical device (e.g., manipulable portion 300 or structure 308) disposed in the interior chamber 603 of the gas removal apparatus 600 while the gas removal apparatus 600 is arranged in the second orientation to effect removal of gas bubbles from the at least the part of the medical device due to an interaction between the at least the part of the medical device and provided liquid present in the interior chamber 603 of the gas removal apparatus 600. According to various embodiments, the at least part of the medical device (e.g., manipulable portion 300) is flushed of gas bubbles as per block 706. In various embodiments, gas bubbles are removed from the at least part of the medical device (e.g., manipulable portion 300 or structure 308) while the at least the part of the medical device is in a deployed configuration to expose a greater amount (e.g., a greater amount of surface area) of the part of the medical device to the flushing action and reduce the presence of crevices and other surface disruptions capable of entrapping or otherwise being a focal point for the presence of undesired fluid (e.g., air bubbles or other gaseous bubbles). In some embodiments, the at least part of the medical device (e.g., manipulable portion 300 or structure 308) may be translated or reciprocated axially along an axis of second opening 614 to affect the removal of the gas bubbles. Here, "removal" of the gas bubbles includes the case where all visible gas bubbles are removed from the at least part of the medical device (e.g., manipulable portion 300 or structure 308), but it does not necessarily require that all gas bubbles are removed from the at least part of the medical device (e.g., manipulable portion 300 or structure 308). For example, "removal" of the gas bubbles includes the case where a small number of gas bubbles, which may not be visible, remain after block 706 of method 700 is performed.

Block 708 of method 700 includes, according to various embodiments, moving, after the moving (i.e., as per block 706) of the at least part of the medical device (e.g., manipulable portion 300 or structure 308), the gas removal apparatus 600 from the second orientation to a third orientation different from the second orientation. For example, in some embodiments, the third orientation may be similar to or the same as the first orientation (e.g., an orientation associated with liquid receiving position 616). In some embodiments in which the at least part of the medical device (e.g., manipulable portion 300 or structure 308) is present in the interior chamber 603 of the gas removal apparatus 600 during the movement of the gas removal apparatus 600 from the second orientation to the third orientation, the third orientation may be a particular orientation in which the at least part of the medical device may not be totally submerged in the liquid (e.g., provided as per block 702) in the interior chamber 603 of the gas removal apparatus 600 when the gas removal apparatus 600 is in the third orientation. According to some embodiments, the gas removal apparatus 600 may include a second opening (e.g., 614) other than the first opening (e.g., 607) that is fully positioned below an uppermost surface of the liquid (e.g., provided as per block 702) in the interior chamber 603 of the gas removal apparatus 600 when the gas removal apparatus 600 is in the second orientation. According to some embodiments, the third orientation may be a particular orientation in which at least part of the second opening (e.g., 614) may be located above an uppermost surface of the liquid in the interior chamber 603 of the gas removal apparatus 600 when the gas removal apparatus 600 is in the third orientation. In some embodiments, the second opening may be positioned to permit a lesser outflow, via the second opening, of the liquid (e.g., provided as per block 702) from the interior chamber 603 of the gas removal apparatus 600 when the gas removal apparatus 600 is in the third orientation than when the gas removal apparatus 600 is in the second orientation. Accordingly, in some embodiments, the third orientation may be selected to reduce spillage of the liquid contained in the interior chamber 603 of the gas removal apparatus 600, which is typically an important factor at a clinical site.

It is noted that the third orientation of the gas removal apparatus 600 includes any and all orientations or positions of the gas removal apparatus 600 that the gas removal apparatus 600 may be moved to and that differ from the second orientation. The embodiments of FIGS. 4C and 4E each depict one example of an orientation or position of the gas removal apparatus 600 that the gas removal apparatus 600 may be moved to and that differ from the second orientation. As noted above, in some embodiments, the third orientation may differ from the first orientation (e.g., an orientation associated with liquid receiving position 616). In other embodiments, the third orientation may be the same as, or substantially similar to, the first orientation. In some embodiments, (a) the gas removal apparatus 600 is supported by a first object while arranged in the first orientation, or (b) the gas removal apparatus 600 is supported by a second object while arranged in the second orientation, or (c) the gas removal apparatus 600 is supported by a third object while arranged in the third orientation, or (a) and (b), or (a) and (c), or (b) and (c), or (a), (b), and (c). In some embodiments, (d) the first object and the second object are the same object, or (e) the first object and the third object are the same object, or (f) the second object and the third object are the same object, or (g) the first object, the second object and the third object are the same object. According to various embodiments, the gas removal apparatus 600 may be supported by various supporting objects in various manners in each of the first orientation, the second orientation and the third orientation. For example, in some embodiments, the gas removal apparatus may be gripped (for example via a supporting object such as a user's hand or a mechanical clamping device) in any one of the first orientation, the second orientation, and the third orientation. In some embodiments, the gas removal apparatus 600 may be suspended (for example hung or suspended from an overhead supporting object or device) in any one of the first orientation, the second orientation or the third orientation. In some embodiments, the gas removal apparatus 600 may be supported on (for example, supported by an underlying supporting object or device) in any one of the first orientation, the second orientation or the third orientation. In some embodiments, a side of the gas removal apparatus 600 (e.g., the one or more second contact surfaces 624 or surface 626) may be coupled to a structure that supports the gas removal apparatus 600 in, and allows for movement of the gas removal apparatus 600 to, any one of the first orientation, the second orientation or the third orientation. In some embodiments, the gas removal apparatus 600 is indirectly or directly grasped or otherwise handled by a user in a manner that allows for movement of the gas removal apparatus 600 to any one of the first orientation, the second orientation or the third orientation. In some embodiments, (d) the gas removal apparatus 600 may be arranged on the first object while arranged in the first orientation, (e) the gas removal apparatus 600 may be arranged on the second object while arranged in the second orientation, or (f) the gas removal apparatus 600 may be arranged on the third object while arranged in the third orientation, or (d) and (e), or (d) and (f), or (e) and (f), or (d), (e), and (f). For example, the gas removal apparatus 600 may include various contact surface sets (e.g., the first set of one more contact surfaces 622, the second set of one or more contact surfaces 624) configured to be supported by an underlying object or objects in at least one of the first orientation, the second orientation or the third orientation. In some embodiments, a different set of one or more contact surfaces of the gas removal apparatus 600 are supported on an underlying object or objects in at least two of the first orientation, the second orientation and the third orientation. For example, the gas removal apparatus 600 may be configured such that the first set of one or more contact surfaces 622 are arranged to be supported on an underlying object in the first orientation (e.g., FIGS. 4C, 4E) and the second set of one more contact surfaces 624 are arranged to be supported on an underlying object in the second orientation (e.g., FIGS. 4D, 4F). In some embodiments, a same set of one or more contact surfaces of the gas removal apparatus 600 are supported on an underlying object or objects in at least two of the first orientation, the second orientation, and the third orientation. For example, the gas removal apparatus 600 may be configured such that the first set of one or more contact surfaces 622 are arranged to be supported on an underlying object in the first orientation and in the third orientation.

Block 710 of method 700 includes, according to various embodiments, removing the at least the part of the medical device (e.g., manipulable portion 300 or structure 308) from the interior chamber 603 of the gas removal apparatus 600. According to various embodiments, the at least part of the medical device (e.g., manipulable portion 300 or structure 308) may be removed from the interior chamber 603 of the gas removal apparatus 600 via a second opening (e.g., 614) other than the first opening (e.g., 607) provided in the gas removal apparatus 600.

In some embodiments, the removing the at least part of the medical device (e.g., manipulable portion 300 or structure 308) from the interior chamber 603 of the gas removal apparatus 600 as per block 710 includes removing the at least the part of the medical device (e.g., manipulable portion 300 or structure 308) from the interior chamber 603 of the gas removal apparatus 600 when the gas removal apparatus 600 is in the third orientation. For example, in some embodiments in which the at least the part of the medical device (e.g., manipulable portion 300 or structure 308) is removed from the interior chamber 603 of the gas removal apparatus 600 via second opening 614, removal of the at least the part of the medical device (e.g., manipulable portion 300 or structure 308) while the gas removal apparatus 600 is in the second orientation may be associated with an undesired leakage of the liquid from the interior chamber 603 as the at least the part of the medical device is withdrawn from the interior chamber 603 via the second opening 614. Removal of the at least the part of the medical device (e.g., manipulable portion 300 or structure 308) from the interior chamber 603 via the second opening 614 when the gas removal apparatus 600 is in the third orientation may be employed to reduce the amount of liquid leakage during the removal of the at least the part of the medical device (e.g., manipulable portion 300 or structure 308).

In some embodiments, the removing of the at least the part of the medical device (e.g., manipulable portion 300 or structure 308) from the interior chamber 603 of the gas removal apparatus 600 may include retracting the at least the part of the medical device (e.g., manipulable portion 300 or structure 308) via the second opening 614 into a fluid vessel physically coupled to the gas removal apparatus 600. For example, FIGS. 4H, 4I and 4J show a sequence of actions in which the at least part of the medical device is delivered into the interior chamber 603 of the gas removal apparatus 600 via loading assembly 640 which is physically (e.g., detatchably) coupled to the gas removal apparatus 600 at a location at least proximate to the second opening 614. In this sequence of actions, the at least the part of the medical device (e.g., manipulable portion 300 or structure 308) is delivered from the fluid vessel 650 of the loading assembly 640 through the second opening 614 of the gas removal apparatus 600 into the interior chamber 603 of the gas removal apparatus 600. According to various embodiments, the at least the part of the medical device (e.g., manipulable portion 300 or structure 308) may undergo a change in configuration from a first configuration in which the at least the part of the medical device is sized for delivery through at least the fluid vessel 650 of the loading assembly 640 to at least a second configuration in which the at least the part of the medical device is sized too large for delivery through at least the fluid vessel 650 of the loading assembly 640. In a similar manner, a reversal of the sequence of the delivery of the at least the part of the medical device (e.g., manipulable portion 300 or structure 308) from the fluid vessel 650 into the interior chamber 603 as shown in FIGS. 4H, 4I and 4J may be used to represent a retraction or removal of the at least the part of the medical device (e.g., manipulable portion 300 or structure 308) from the interior chamber 603 of the gas removal apparatus 600 into the attached fluid vessel 650 according to various embodiments. It is noted that although no liquid is shown in the interior chamber 603 in FIGS. 4H, 4I and 4J, such liquid may be present in the interior chamber 603 during the retraction or removal of the at least the part of the medical device (e.g., manipulable portion 300 or structure 308) from the interior chamber 603 of the gas removal apparatus 600 into the attached fluid vessel 650 according to various embodiments. In some embodiments, liquid may be present in each of the interior chamber 603 and the attached fluid vessel 650 during the retraction or removal of the at least the part of the medical device (e.g., manipulable portion 300 or structure 308) from the interior chamber 603 of the gas removal apparatus 600 into the attached fluid vessel 650. In some embodiments, the at least the part of the medical device (e.g., manipulable portion 300 or structure 308) may be fully submerged in liquid throughout the retraction or removal of the at least the part of the medical device from the interior chamber 603 of the gas removal apparatus 600 into the attached fluid vessel 650. Total submersion of the at least the part of the medical device in fluid throughout the retraction or removal of the at least the part of the medical device may be employed to avoid exposing the at least the part of the medical device to air or other undesired fluids throughout the retraction or removal of the at least the part of the medical device.

In some embodiments, the retraction of the at least the part of the medical device (e.g., manipulable portion 300 or structure 308) into the fluid vessel 650 occurs after undesired gas bubbles are removed from the at least the part of the medical device (e.g., manipulable portion 300 or structure 308) (for example, as per block 706). In some embodiments, during the retraction, the at least the part of the medical device (e.g., manipulable portion 300 or structure 308) may undergo a change in configuration from a second configuration in which the at least the part of the medical device is sized too large for delivery through at least the fluid vessel 650 of the loading assembly 640 to at least a first configuration in which the at least the part of the medical device is sized to be deliverable through at least the fluid vessel 650 of the loading assembly 640. According to some embodiments, method 700 may include decoupling the fluid vessel 650 from the gas removal apparatus 600 after the retracting the at least part of the medical device (e.g., manipulable portion 300 or structure 308). Decoupling of the fluid vessel 650 from the gas removal apparatus 600 (e.g., via a decoupling of the loading assembly 640) may be motivated by various reasons. For example, it may be desired to subsequently couple the fluid vessel 650 to a catheter sheath (e.g., 312) for delivery of the flushed the at least the part of the medical device (e.g., manipulable portion 300 or structure 308) into the body via the catheter sheath. According to some embodiments, retraction of the at least the part of the medical device (e.g., manipulable portion 300 or structure 308) from the interior chamber 603 of the gas removal apparatus 600 into to the fluid vessel 650 may accompany a transfer of at least some of the liquid from the interior chamber 603 to the fluid vessel 640. In some embodiments, liquid is present in the fluid vessel 650 during retraction of the at least the part of the medical device (e.g., manipulable portion 300 or structure 308) from the interior chamber 603 of the gas removal apparatus 600 into to the fluid vessel 650.

According to some embodiments, the retracting the at least the part of the medical device (e.g., manipulable portion 300 or structure 308) via the second opening 614 into the fluid vessel 650 coupled to the gas removal apparatus 600 occurs when the gas removal apparatus is arranged in the second orientation (e.g., an orientation associated with the another position 618, FIGS. 4D, 4F). It is noted that according to some embodiments, the coupled fluid vessel 650 may limit liquid leakage from the interior chamber 603 during the retraction of the at least the part of the medical device (e.g., manipulable portion 300 or structure 308) from the interior chamber 603 of the gas removal apparatus 600 even when the gas removal apparatus 600 is in a particular orientation (e.g., an orientation associated with the another position 618) in which the second opening 614 is well below the uppermost surface of the liquid in the interior chamber (i.e., a condition that could lead to a great deal of leakage in the absence of the attached fluid vessel 650). According to various embodiments, it may be desired to retract or otherwise remove the at least the part of the medical device (e.g., manipulable portion 300 or structure 308) from the interior chamber 603 of the gas removal apparatus 600 when the gas removal apparatus 600 is in a particular position and orientation (e.g., the another position 618) in which the at least part of the medical device is below (e.g., totally submerged) the uppermost surface of the liquid in the interior chamber 603 of the gas removal apparatus 600 as opposed to a condition in which gas removal apparatus 600 is in a particular position and orientation (e.g., the liquid receiving position 616) in which at least a portion the at least part of the medical device is above the uppermost surface of the liquid in the interior chamber 603 which can needlessly expose the at least part of the medical device to an environment that can lead to the formation of additional gas bubbles.

According to some embodiments, the decoupling the fluid vessel (e.g. 650) from the gas removal apparatus 600 occurs when the gas removal apparatus 600 is arranged in an orientation other than the second orientation. According to some embodiments, the decoupling the fluid vessel (e.g. 650) from the gas removal apparatus 600 occurs after the moving the gas removal apparatus 600 from the second orientation to the third orientation. Decoupling the fluid vessel (e.g. 650) from the gas removal apparatus 600 when the gas removal apparatus 600 is in an orientation other than the second orientation may be motivated for different reasons. For example, if the fluid vessel (e.g., 650) were decoupled from the gas removal apparatus 600 while the gas removal apparatus was positioned in the second orientation (exemplified in FIGS. 4D, 4E), it could potentially lead to a relatively large amount of undesired liquid leakage as the second opening 614 is well below the uppermost surface of the liquid in the interior chamber 603 of the gas removal apparatus 600. Conversely, if the fluid vessel (e.g., 650) were decoupled from the gas removal apparatus 600 while the gas removal apparatus was positioned in a particular orientation other than the second orientation (e.g., a particular orientation exemplified in FIGS. 4C, 4E), it would lead to relatively low amounts of liquid leakage. According to some embodiments, the at least a part of the medical device (e.g., manipulable portion 300 or structure 308) is retracted into the fluid vessel (e.g., 650) when the gas removal apparatus 600 is oriented to maximized exposure of the at least a part of the medical device to liquid in the interior chamber 603 of the gas removal apparatus 600 (e.g., to minimize exposure of the at least a part of the medical device to a gaseous environment), and the fluid vessel (e.g., 650) containing the at least a part of the medical device is decoupled from the gas removal assembly 600 while the gas removal assembly is positioned with an orientation that reduces the amount of possible liquid leakage via the second opening resulting from the decoupling.

While some of the embodiments disclosed above are suitable for the flushing of various instruments employed in cardiac mapping or ablation, the same or similar embodiments may be used for flushing various instruments used in the treatment or diagnosis or other bodily organs or any bodily lumen, bodily chamber or bodily cavity. For example, although manipulable portions 200 and 300 are often described herein as transducer-based devices, the invention is not limited to flushing of transducer-based devices, and other forms of catheter-based manipulable portions (e.g., a stent or other implant) may be utilized.

The gas removal apparatus 600 may be made of various materials, singly or in combination. According to some embodiments, the gas removal apparatus 600 is made of one or more materials that allow a user to see inside the gas removal apparatus 600 so that the user can see the at least a part of the medical device (e.g., manipulable portion 300 or structure 308) disposed inside the interior chamber 603. According to one embodiment, the gas removal apparatus 600 is made of one or more transparent materials. According to another embodiment, the gas removal apparatus 600 is made of one or more transparent plastic materials.

Subsets or combinations of various embodiments described above can provide further embodiments.

These and other changes may be made to the invention in light of the above-detailed description. In general, in the following claims, the terms used should not be construed to limit the invention to the specific embodiments disclosed in the specification and the claims. In this regard, the invention is not limited by the disclosure, but instead its scope is to be determined entirely by the following claims.

What is claimed is:

1. A gas removal apparatus configured to receive a first amount of liquid effective to remove gas bubbles from at least a part of a medical device removably disposed in the gas removal apparatus, the gas removal apparatus comprising:
    an interior chamber configured to hold the at least the first amount of liquid; and
    a wall portion comprising a first surface and a second surface opposite across a thickness of the wall portion from the first surface, the first surface of the wall portion being configured to receive at least the first amount of liquid and cause the received at least the first amount of liquid to flow along the first surface of the wall portion to the interior chamber when the gas removal apparatus is arranged in a liquid receiving position, and the second surface of the wall portion defining at least part of the interior chamber,
    wherein at least a portion of the second surface of the wall portion is configured to, when the gas removal apparatus is arranged in the liquid receiving position in a state where the at least the first amount of liquid is present in the interior chamber, not contact the at least the first amount of liquid present in the interior chamber, and
    wherein the at least the portion of the second surface of the wall portion is configured to, when the gas removal apparatus is arranged in another position different from the liquid receiving position in the state where the at least the first amount of liquid is present in the interior chamber, contact the at least the first amount of liquid present in the interior chamber.

2. The gas removal apparatus of claim 1, further comprising:
    one or more first contact surfaces configured to contact a supporting object when the gas removal apparatus is arranged in the liquid receiving position while supported by the supporting object; and
    one or more second contact surfaces configured to contact the supporting object when the gas removal apparatus is arranged in the another position different from the liquid receiving position while supported by the supporting object.

3. The gas removal apparatus of claim 2, wherein each of at least one surface of the one or more first contact surfaces opposes the second surface of the wall portion across the interior chamber.

4. The gas removal apparatus of claim 2, comprising a first opening arranged at an end of the wall portion and configured to provide a first path into the interior chamber, the first surface of the wall portion configured such that the received at least the first amount of liquid caused to flow along the first surface of the wall portion to the interior chamber when the gas removal apparatus is arranged in the liquid receiving position enters the interior chamber via the first path provided by the first opening,
    wherein the first opening is an elongated opening arranged between the end of the first surface of the wall portion and one or more third surfaces of the gas removal apparatus such that the liquid flowing along the first surface of the wall portion enters the interior chamber via the elongated opening.

5. The gas removal apparatus of claim 4, wherein at least some of the received at least the first amount of liquid caused to flow along the first surface of the wall portion and enter the interior chamber via the elongated opening is then caused to flow along at least a portion of at least one third surface of the one or more third surfaces of the gas removal apparatus.

6. The gas removal apparatus of claim 2, wherein the first surface of the wall portion, the second surface of the wall portion, or each of both the first surface of the wall portion and the second surface of the wall portion has a sloped orientation relative to a) each of at least one of the one or more first contact surfaces, b) each of at least one of the one or more second contact surfaces, or both a) and b).

7. The gas removal apparatus of claim 2, wherein (a) the first surface of the wall portion, the second surface of the wall portion, or each of both the first surface of the wall portion and the second surface of the wall portion slopes toward each of at least one surface of the one or more first contact surfaces as the wall portion extends upward when the gas removal apparatus is arranged in the another position different from the liquid receiving position while supported by the supporting object, (b) each of at least one surface of the one or more first contact surfaces slope toward the first surface of the wall portion, the second surface of the wall portion, or each of both the first surface of the wall portion and the second surface of the wall portion as the one or more first contact surfaces extend upward when the gas removal apparatus is arranged in the another position different from the liquid receiving position while supported by the supporting object, or both (a) and (b).

8. The gas removal apparatus of claim 2, wherein another wall portion comprises the one or more first contact surfaces and a third surface opposite across a thickness of the another wall portion from the one or more first contact surfaces, the third surface of the another wall portion defining at least part of the interior chamber, and wherein the first surface of the wall portion, the second surface of the wall portion, or each of both the first surface of the wall portion and the second surface of the wall portion is configured to be out of plumb by a first angular amount when the gas removal apparatus is arranged in the another position different from the liquid receiving position on a level surface, and wherein the third surface of the another wall portion is configured to be out of plumb by a second angular amount when the gas removal apparatus is arranged in the another position different from the liquid receiving position on the level surface.

9. The gas removal chamber of claim 8, wherein the first angular amount is substantially equal to the second angular amount.

10. The gas removal chamber of claim 8, wherein the first angular amount varies by no more than twenty percent of the second angular amount or the second angular amount varies by no more than twenty percent of the first angular amount.

11. The gas removal apparatus of claim 2, wherein another wall portion comprises the one or more first contact surfaces and a third surface opposite across a thickness of the another wall portion from the one or more first contact surfaces, the third surface of the another wall portion being opposite across the interior chamber from the second surface of the wall portion, and wherein the first surface of the wall portion, the second surface of the wall portion, or each of both the first surface of the wall portion and the second surface of the wall portion is configured to be out of plumb by a first angular amount when the gas removal apparatus is arranged in the another position different from the liquid receiving position on a level surface, and wherein the third surface of the another wall portion is configured to be out of plumb by a second angular amount when the gas removal apparatus is arranged in the another position different from the liquid receiving position on the level surface.

12. The gas removal apparatus of claim 2, wherein the first surface of the wall portion, the second surface of the wall portion, or each of both the first surface of the wall portion and the second surface of the wall portion is configured to be out of level by a first angular amount when the gas removal apparatus is in the liquid receiving position on a level surface, and wherein at least one surface of the one or more second contact surfaces is configured to be out of plumb by a second angular amount when the gas removal apparatus is in the liquid receiving position on the level surface.

13. The gas removal apparatus of claim 12, wherein the first angular amount is different from the second angular amount.

14. The gas removal apparatus of claim 12, wherein a magnitude of the first angular amount is greater than a magnitude of the second angular amount.

15. The gas removal apparatus of claim 12, wherein a magnitude of the first angular amount is nominally twice the magnitude of the second angular amount.

16. The gas removal apparatus of claim 2, wherein the one or more first contact surfaces is/are arranged to contact the supporting object at each of a first set of three or more points of contact when the gas removal apparatus is arranged in the liquid receiving position while supported by the supporting object, and at least three points of contact of the first set of three or more points of contact are arranged non-colinearly.

17. The gas removal apparatus of claim 16, wherein the one or more second contact surfaces is/are arranged to contact the supporting object at each of a second set of three or more points of contact when the gas removal apparatus is arranged in the another position different from the liquid receiving position while supported by the supporting object, and at least three points of contact of the second set of three or more points of contact are arranged non-colinearly.

18. The gas removal apparatus of claim 1, wherein the first surface of the wall portion is an external surface of the gas removal apparatus.

19. The gas removal apparatus of claim 1, comprising a first opening arranged at an end of the wall portion and configured to provide a first path into the interior chamber, the first surface of the wall portion configured such that the received at least the first amount of liquid caused to flow along the first surface of the wall portion to the interior chamber when the gas removal apparatus is arranged in the liquid receiving position enters the interior chamber via the first path provided by the first opening.

20. The gas removal apparatus of claim 19, comprising a second opening configured to provide a second path into the interior chamber and configured to receive the medical device such that the at least the part of the medical device enters the interior chamber via the second path provided by the second opening, the first path into the interior chamber and the second path into the interior chamber being mutually exclusive paths into the interior chamber.

21. The gas removal apparatus of claim 20, wherein a shape of the first opening is different from a shape of the second opening.

22. The gas removal apparatus of claim 19, wherein the first opening is an elongated opening.

23. The gas removal apparatus of claim 1, wherein the gas removal apparatus is configured such that, when arranged in the liquid receiving position in the state where the at least the first amount of liquid is present in the interior chamber, the first surface of the wall portion, the second surface of the wall portion, or each of both the first surface of the wall portion and the second surface of the wall portion has a sloped orientation relative to an uppermost surface of the at least the first amount of liquid present in the interior chamber.

24. The gas removal apparatus of claim 1, wherein no portion of the second surface of the wall portion is configured to, when the gas removal apparatus is arranged in the liquid receiving position in a state where the at least the first amount of liquid is present in the interior chamber, contact the at least the first amount of liquid present in the interior chamber.

25. The gas removal apparatus of claim 1, wherein the second surface of the wall portion and an interior surface opposite across a thickness of the one or more first contact surfaces oppose each other for a first distance, and
    a second distance between the second surface of the wall portion and the interior surface increases as at least part of the first distance is traversed away from an opening arranged at an end of the wall portion and configured to provide a first path into the interior chamber.

\* \* \* \* \*